US012569454B2

(12) United States Patent
Lopachin et al.

(10) Patent No.: US 12,569,454 B2
(45) Date of Patent: Mar. 10, 2026

(54) NUCLEOPHILIC CHEMICALS USEFUL IN THE TREATMENT OF CISPLATIN-INDUCED SENSORY NEUROPATHY AND OTOTOXICITY

(71) Applicant: MONTEFIORE MEDICAL CENTER, Bronx, NY (US)

(72) Inventors: Richard Lopachin, New York, NY (US); Brian C. Geohegan, New York, NY (US)

(73) Assignee: MONTEFIORE MEDICAL CENTER, Bronx, NY (US)

(*) Notice: Subject to any disclaimer, the term of this patent is extended or adjusted under 35 U.S.C. 154(b) by 598 days.

(21) Appl. No.: 17/309,702

(22) PCT Filed: Dec. 27, 2019

(86) PCT No.: PCT/US2019/068734
§ 371 (c)(1),
(2) Date: Jun. 15, 2021

(87) PCT Pub. No.: WO2020/140029
PCT Pub. Date: Jul. 2, 2020

(65) Prior Publication Data
US 2022/0016051 A1    Jan. 20, 2022

Related U.S. Application Data

(60) Provisional application No. 62/785,292, filed on Dec. 27, 2018.

(51) Int. Cl.
| | |
|---|---|
| *A61P 25/28* | (2006.01) |
| *A61K 31/12* | (2006.01) |
| *A61K 31/122* | (2006.01) |
| *A61K 31/167* | (2006.01) |
| *A61K 31/282* | (2006.01) |
| *A61K 33/243* | (2019.01) |
| *A61P 35/00* | (2006.01) |

(52) U.S. Cl.
CPC ............ *A61K 31/122* (2013.01); *A61K 31/12* (2013.01); *A61K 31/167* (2013.01); *A61K 31/282* (2013.01); *A61K 33/243* (2019.01); *A61P 25/28* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 7,022,315 B2 | 4/2006 | Neuwelt et al. | |
| 2007/0105782 A1* | 5/2007 | Campbell | A61K 38/063 514/17.7 |
| 2016/0074339 A1* | 3/2016 | LoPachin | A61K 31/4015 568/376 |

OTHER PUBLICATIONS

Gupta et al. (Understanding the routes of administration, Handbook of Space Pharmacueticals, available online Oct. 27, 2018). (Year: 2018).*
Zajaczkowska et al. (Mechansims of Chemotherapy-Induced Peripheral Neuropathy, Int J Mol Sci Mar. 2019; 20(6): 1451. (Year: 2019).*
Landier (Ototoxicity and cancer therapy, Cancer, An International Interdisciplinary Journal of the American Cancer Society, Feb. 9, 2016) (Year: 2016).*
Lopachin et al. (Enolate-Forming Compounds as a Novel Approach to Cytoprotection, Chemical Research in Toxicology, 2016, 29, 2096-2107) (Year: 2016).*
Rybak et al. 'Mechanism of Protection by Diethyldithiocarbamate against Cisplatin Ototoxicity: Antioxidant System', Fundamental and Applied Toxicology, 1995, vol. 26, pp. 293-300. p. 299, col. 1, para 2.
Travis et al. 'Chemotherapy-Induced Peripheral Neurotoxicity and Ototoxicity: New Paradigms for Translational Genomics', JNCI J. Natl. Cancer Inst. 2014, vol. 106(5), pp. 1-11.
International Search Report and Written Opinion for PCT/US19/068734, dated Feb. 12, 2020, 9 pages.
Avan A, Postma TJ, Ceresa C, Avan A et al. (2015) Platinum-induced neurotoxicity and preventive strategies: past, present and Future. The Oncol 20: 411-432.
Begum, A.N., Jones, M.R., Lim, G.P et al. (2008) Curcumin structure-function, bioavailability and efficacy in models of neuroinflammation and Alzheimer's disease. J. Pharamacol. Exp. Ther. 326, 196-208.
Berndtsson M, Hagg M, Panaretakis T, Havelka AM, Shoshan MC, Linder S. (2006) Acute apoptosis by cisplatin requires induction of reactive oxygen species but is not associated with damage to nuclear DNA. Int. J. Cancer 120: 175-180.
Brock PR, Knight KR, Freyer DR (2012) Platinum-induced ototoxicity in children: a consensus review on mechanism predisposition and protection, including a new international society of pediatric oncology Boston ototoxicity scale. J. Clin. Oncol. 30: 2408-2417.
Carozzi VA, Canta A and Chiorzaai A. (2015) Chemotherapy-induced peripheral neuropathy: What do we know about mechanism? Neurosci. Lett. 596: 90-107.
Cece R, Petruccioli MG, Cavletti G, Barajon I , Tredici G (1995) An ultrastructural study of neuronal changes in dorsal root ganglia (DRG) of rats after chronic cisplatin administration. Histo. Histopathol. 10: 837-845.
Dedon PC, Borch RF. (1987) Characterization of the reactions of platinum antitumor agents with biologic and nonbiologic sulfur-containing nucleophiles. Biochem. Pharamcol. 36: 1955- 1964.
DePascali SA, Papadia P, Ciccarese A, Pacifico C and Fanizzi FP (2005) First Examples of ß- Diketonate Platinum(II) Complexes with Sulfoxide Ligands. Eurp. J. Inorg. Chem. 5: 788-796.
Fuertes MA, Alonso CJ, Perez JM. (2003) Cisplatin biochemical mechanism of action: from cytotoxicity to induction of cell death through interconnections between apoptotic and necrotic pathways. Curr. Med. Chem. 10: 257-266.
Gaona-Gaona L, Molina-jijon E, Tapia E, Zazueta C, Hernandez-Pando R, Clderon-Oliver M, Zarco-Marquez G, Pinzon E , Pedraza-Chaverri J. (2011). Protective effect of sulforaphane pretreatment against cisplatin-induced liver and mitochondrial oxidant damage in rats. Toxicology 286: 20-27.

(Continued)

*Primary Examiner* — Melissa S Mercier
(74) *Attorney, Agent, or Firm* — Perkins Coie LLP

(57) ABSTRACT
Methods and compositions are disclosed for reducing neuropathy or ototoxicity associated with chemotherapeutic agents by administering one or more enol compounds to a subject.

9 Claims, 6 Drawing Sheets

(56)                    References Cited

OTHER PUBLICATIONS

Geohagen BC, Korsharskyy B, Vydyanatha A, Nordstoem LU and LoPachin RM. (2018) Phloretin pharmacology and Toxicity. Chem. Biol. Inter. 296: 117-123.

Geohagen BC, Vydyanathan A, Kosharskyy B, Shaparin N, Gavin T and LoPachin RM. (2016) Enolate-forming phioretin pharmacophores: Hepatoprotection in an experimental model of drug-induced toxicity. J. Pharmacol. Exp. Ther. 357: 476-486.

Jamieson ER, Lippard SJ (1999) Structure, recognition and processing of cisplatin-DNA adducts. Chem. Rev. 99: 2467-2498.

Kanat O, Ertas H, Caner B (2017) Platinum-induced neurotoxicity: A review of possible mechanisms. World J. Clin. Oncol. 8: 329-335.

Kosharskyy B, Vydyanathan A, Zhang L, Shaparin N, Geohagan BC, Bivin W, Liu Q, Gavin T and LoPachin RM (2015) 2-Acetylcyclopentanone, an Enolate-Forming 1,3-dicarbonyl compound, is Cytoprotective in Warm Ischemia-Reperfusion Injury in Rat Liver. J. Pharmacol. Exp. Ther. 353: 150-158.

Lemaire MA, Schwartz A, Rahmouni R, Leng M. (1991) Interstrad cross-links are preferentially formed at the d(GC) sites in the reaction between cis-diamminedichloroplatinum(II) and DNA. Proc. Nat. Acad. Sci. 88: 1982-1985.

LoPachin RM and Gavin T (2012) Molecular Mechanism of Acrylamide Neurotoxicity: Lessons Learned from Organic Chemistry. Environ. Health 120: 1650-1657.

LoPachin RM and Gavin T (2012) Molecular Mechanisms of Aldehyde Toxicity: A Chemical Perspective. Chem. Res. Toxicol. 27: 1081-1091.

LoPachin RM, Barber DS, Geohagen BC, Gavin T, Das S, He D. (2007) Structure-Toxicity Analysis of Type-2 Alkenes: Synaptosomal Neurotoxicity. Toxicol. Sci. 95, 136-146.

LoPachin RM, Gavin T, DeCaprio AP, Barber DS (2012). Application of the hard and soft, acids and bases (HSAB) theory to toxicant-target interactions. Chem. Res. Toxicol. 25, 231-251.

LoPachin RM, Gavin T, Geohagen BC, Zhang L, Casper D, Lekhraj R, Barber DS. (2011) 0- Dicarbonyi enolates: a new class of neuroprotectants. J. Neurochem. 116, 132-143.

LoPachin RM, Geohagen BC, Gavin T, Das S. (2007) Neurotoxic Mechanisms of Electrophilic Type-2 Alkenes: Soft-Soft Interactions Described by Quantum Mechanical Parameters. Toxicol. Sci. 98: 561-570.

Lopachin, R.M. and Barber, D.S. (2006) Synaptic cysteine sulfhydryl groups as targets of electrophilic neruotoxicants. Tox. Sci. 94, 240-255.

Lopachin, R.M., Barber, D.S. and Gavin, T. (2008). Molecular mechanisms of the conjugated ot,p-unsaturated carbonyl derivatives: relevance to neurotoxicity and neurodegenerative diseases. Tox. Sci. 104, 235-249.

Lopachin, R.M., Gavin, T., and Geohagen, B.C. (2009) Synaptosomal Toxicity and Nucleophilic Targets of 4-Hydroxy-2-Nonenal. Toxicol. Sci. 107, 171-181.

Loudon GM (2002) Chemistry of enolate ions, enols and alpha(3-unsaturated carbonyl compounds. In Organic Chemistry, 4th ed. Chapt. 22, pp. 997-1068. Oxford University Press, NY.

Lu Y and Cederbaum Al (2006) Cisplatin-induced hepatotoxicity is enhanced by elevated expression of cytochrome P450 2E1. Toxicol. Sci. 89: 515-523.

Luo J, Tsuji T, Yasuda H, Sun Y, Fujigaki Y., Hishida Y. (2008). The molecular mechanisms of the attenuation of cisplatin-induced acute renal failure by N-acetylcysteine in rats. Nephrol Dial Transplant 23:2198-2205.

Mandic A, Hansson J, Linder S, Shoshan MC. (2003) Cisplatin induces endoplasmic reticulum stress and nucleus-independent apoptotic signaling. J. Biol. Chem. 278: 9100-9106.

Martyniuk, C.J., Fang, B., Koomen, J.M., Gavin, T., Barber, D.S. and LoPachin, R.M., (2011) Molecular Mechanism of Protein Inactivation by o.,[3-Unsaturated Carbonyl Derivatives. Chem. Res. Toxicol. 24, 2302-2311.

McKeage MJ, Hsu T, Screnci K, Haddad G, Baguley BC. (2001). Nucleolar damage correlates with neurotoxicity induced by different platinum drugs. British J. Cancer 85: 1219-1225.

Muldoon LL, Pagel MA, Droll RA, Brummett RE, Doolittle ND, Zuhowski EG, Egorin MJ and Neuwelt EA (2000) Delayed administration of sodium thiosulfate in animal models reduces platinum ototoxicity without reduction of antitumor activity. Clin. Cancer Res. 6: 309-315.

Muldoon LL, Walker-Rosenfeld SL, Hale C, Purcell SE, Bennett, LC and Neuwelt EA (2001) Rescue from enhanced alkylator-induced cell death with low molecular weight sulfur-containing chemoprotectants. J. Pharmacol Exp Ther. 6: 797-805.

Muscella A, Calabriso N, Vetrugno C, Urso L, Fanizzi FP, De Pascal' SA, Marsigliante S. (2010) Sublethal concentrations of the platinum (II) complex [Pt(O,O'-acac) (7-acac) (DMS)] alter the motility and induce anoikis in MCF-7 cells. Brit. J. Pharmacol. 160: 1362-1377.

Neuwelt EA, Brummett RE, Doolittle ND, Muldoon LL, Kroll RA, Pagel MA, Dojan R, Church V, Remsen LG and Bubalo JS. (1998) First evidence of otoprotection against carboplatin-induced hearing loss with a two-compartment system in patients with central nervous system malignancy using sodium thiosulfate. J. Pharmacol. Exp. Ther. 286: 77-84.

Park SB, Goldstein D, Krishnan AV, Lin CSY, Friedlander ML et al. (2013) Chemotherapy- induced peripheral neurotoxicity: A critical Analysis. 63: 419-437.

Rezk BM, Haenen GRMM, van der Vijgh WJF and Bast A. (2002) The antioxidant activity of phloretin: the disclosure of a new antioxidant pharmacophore in flavonoids. Biochem. Biophys. Res. Comm. 295: 9-13.

Rybak LP, Whitworth CA, Mukherjea and Ramkumar V (2007) Mechanism of cisplatin-induced ototoxicity and prevention. Hearing Res. 226: 157-167.

Seretny M, Currie GL, Sena ES, Ramnarine S, Grant R et al. (2014) Incidence, prevalence and predictors of chemotherapy-induced peripheral neuropathy: A systematic review and meta- analysis. Pain 155: 2461-2470.

Sheikh-Hamad D. (2008) Cisplatin-induced cytotoxicity: is the nucleus relevant? Am. J. Physiol Renal Physiol. 295: F42-F43.

Ta LE, Espeset L, Podratz J, Windebank A. (2006) Neurotoxicity of oxaliplatin and cisplatin of rat dorsal root ganglion neurons correlates with platinum-DNA binding. Neuro. Toxicology 27: 992-1002.

Terhegeen PMAB, Van der Hoop RG, Floot BGJ, Gispen WH. (1989) Cellular distribution of cis-diamminedichloroplatinum(II)-DNA binding in rat dorsal root spinal ganglia: effect of the neuroprotecting peptide ORG.2766. Toxicol. Appl. Pharmacol. 99: 334-343.

Thompson SW, Davis LE, Kornfeld M, Hilgers RD, Standefers JC. (1984) Cisplatin neuropathy: clinical, electrophysiologic, morphologic and toxicologic studies. Cancer 54: 1269-1275.

Tien M, Bucher JR and Aust SD (1982) Thiol-dependent lipid peroxidation. Biochem. Biophys. Res. Comm. 107: 279-285.

Yu F, Megyesi J, Price PM. (2008) Cytoplasmic initiation of cisplatin cytotoxicity. Am. J. Physiol. Renal Pysiol. 295: F44-F52.

Zhang L, Gavin T, Geohagen BC, Liu Q, Downe KJ and LoPachin RM. (2013). Protective properties of 2-acetylcyclopenanone in a mouse model of acetaminophen hepatotoxicity. J. Pharmacol. Exp Ther. 346: 259-269.

Miltenburg NC and Boogerd W. (2014) Chemotherapy-induced neuropathy: a comprehensive survey. Can. Treat. Rev. 40: 872-882.

Carozzi VA, Marmiroli P, Cavaletti G. (2010). The role of oxidative stress and anti-oxidant treatment in platinum-induced peripheral neurotoxicity. Curr. Cancer Drug Targets 10: 670- 682.

Cece R, Petruccioli MG, Pizzini G, Cavletti G, Tredici G (1995) Ultrastructural aspects of DRG satellite cell involvement in experimental cisplatin neuropathy. Submicro. Cytol. Pathol. 27: 417-425.

Omar HA, Mohamed WR, Arafa SA, Shehata BA, El Sherbiny GA, Arab HH and Elgendy AN (2016) Hesperiden alleviates cisplatin-induced hepatotoxicity in rats without inhibition of its antitumor activity. Pharmacol. Rep. 68: 349-356.

Ballantyne B, Cawley TJ (2001) 2,4-Pentanedione: toxicology update. J. Appl. Toxicol. 21, 165-171.

Beaty, J.A. and Jones, M.M. (1992) Rates of substitution by sulfur nucleophiles in cis- diamminebis (quanosine) platinum (II) chloride. Inorg. Chem. 31: 2547-2551.

(56)        References Cited

OTHER PUBLICATIONS

Bug T and Mayr H (2003) Nucleophilic reactivities of carbonations in water: the unique behavior of the malodinitrile anion. J. Am. Soc. Chem. 125, 12980-12986.

Cavaletti G, Tredici G, Marmiroli P, Petruccioloi MG, Barajon I, Fabbrica D. (1992) Morphometric study of the sensory neuron and peripheral nerve changes induced by chronic cisplatin (DDP) administration in rats. Acta. Neuropathol. 84:364-371.

Cervellini I, Bello E, Frapolli R, Porretta-Serapiglia C, Oggioni N et al. (2110) The neuroprotective effect of erythropoietin in docetaxel-induced peripheral neuropathy causes No. reduction of antitumor activity in 13762 adenocarcinoma-bearing rats. Neurotox. Res. 18: 151- 160.

Eames J (2009) Acid-base properties of enols and enolates. The Chemistry of Metal Enolates (Zablicky J ed) Chapter 8, pp. 411-460. John Wiley & Sons, West Sussex, England.

Feghali JG, Liu W, Van de Water TR. (2001) L-N-acetyl-cysteine protection aginast cisplatin- induced auditory neuronal and hair cell toxicity. The Laryngoscope 111: 1147-1155.

Gandara DR, Wiebe VJ, Perez EA, Makuch RW and DeGregorio MW (1990) Cisplatin rescue therapy: experience with sodium thiosulfate, WR2721 and diethyldithiocarbamate. Crit. Rev Oncol/Hematol 10: 353-365.

Sorenson CM, Eastman A. (1988). Mechanism of cis-diamminedichloroplatinum (II)-induced cytotoxicity: role of G2 arrest and DNA double-strand breaks. Cancer Res. 48: 4484-4488.

Tomiwa, K, Nolan C, Cavanagh JB. (1986) The effects of cisplatin on rat spinal ganglia: a study by light and electron microscopy and by morphometry. Acta. Neuropath. 69: 295-308.

Wang K, Lu J, Li R. (1996) The events that occur when cisplatin encounters cells. Coordin. Chem. Rev. 151: 53-88.

Will, J., Wolters, DA, Sheldrick, WS (2008) Characterisation of cisplatin binding sites in human serum proteins using hyphenated multidimensional liquid chromatography and ESI tandem mass spectrometry. Chem. Med. Chem., 3: 1696-1707.

Wolters DA, Washburn MP, Yates Jr, Iii (2001) An automated multidimensional protein identification technology for shotgun proteomics. Anal. Chem. 73: 5683-5690.

LoPachin RM, Geohagen BC, Nordstrom LU and Gavin T. (2016) Enolate-forming compounds as a novel approach to cytoprotection. Chem. Res. Toxicol. 29: 2096-2107.

Callejo A, Durochat A, Bressieux S, Saleur A et al. (2017) Dose-dependent cochlear and vestibular toxicity of tran-tympaic cisplatin in the rat. Neurotoxicology 60: 1-9.

Reedijk J (1999) Why does cisplatin reach guanine-N7 with competing S-donor ligands available in the cell? Chem. Rev. 99: 2499-2510.

Bazzini p. and Wermuth CG in The Practice of Medicinal Chemistry 2015 4th Edition, Chapter 13, pp. 319-357.

Pinata 0, Musetti C and Sissi C (2014) Pt-Based Drugs: The Spotlight Will be on Proteins. Metallomics 6: 380-395.

* cited by examiner

FIG. 1C

NAHA

FIG. 1D

GAVINOL

FIG. 1A

2-ACP

FIG. 1B

THA

NUCLEOPHILIC CHEMICALS USEFUL IN THE TREATMENT OF CISPLATIN-INDUCED SENSORY NEUROPATHY AND OTOTOXICITY

PRIORITY

This application is a 371 National Phase Application of PCT Application No. PCT/US2019/068734 entitled "NUCLEOPHILIC CHEMICALS USEFUL IN THE TREATMENT OF CISPLATIN-INDUCED SENSORY NEUROPATHY AND OTOTOXICITY" filed on Dec. 27, 2019, which claims priority to U.S. Provisional Application No. 62/785,292 filed on Dec. 27, 2018, the entire contents of which are incorporated herein by reference.

STATEMENT REGARDING FEDERALLY SPONSORED RESEARCH

This invention was made with government support under Grant Number ES003830 awarded by the National Institutes of Health. The government has certain rights in this invention.

BACKGROUND

Cisplatin (CisPt) and other platinum (Pt)-based antineoplastic drugs (e.g., carboplatin (CarboPt), oxaliplatin (OxaliPt)) are highly effective and widely used in the treatment of solid tumors in both children and adult patients. The antineoplastic mechanism of CisPt involves formation of intrastrand cross-links that disrupt the DNA helical structure necessary for transcription (1-3). This initiates apoptotic cell death through DNA damage-recognition pathways. Although considered to be a life-saving chemotherapy, CisPt use is frequently associated with toxicity (50%-60%). Specifically in adults, treatment is accompanied by irreversible injury of sensory dorsal root ganglion (DRG) neurons (1,2-7). The signs and symptoms of this neurotoxicity are sensory-based and include tingling, paresthesia, neuropathic pain and loss of vibratory sense. In children, CisPt chemotherapy is linked to hearing deficits (e.g., ototoxicity) mediated by irreversible damage to outer hair cells. Hearing loss in children can lead to social stunting and learning disorders (8,9). Depending upon the severity of intoxication, CisPt neurotoxicity can be therapy-limiting, which can complicate tumor management and lead to a poor clinical prognosis (2,10).

In this regard, initial experimental research showed that thiol nucleophiles such as N-acetyl cysteine (NAC) and sodium thiosulfate (STS) could prevent CisPt neurotoxicity without disrupting antineoplastic efficacy. However, despite encouraging pre-clinical findings, no effective pharmacological strategies were identified in human trials due to low therapeutic efficacy and sulfur radical-mediated toxicity. The development of an efficacious neuroprotectant is therefore an unmet clinical need.

SUMMARY

The application relates to compositions comprising enol compounds for treating and/or preventing chemotherapeutic-induced neuropathy and/or ototoxicity.

In some aspects, the present disclosure provides methods of treating or preventing chemotherapy-induced neuropathy and ototoxicity in a subject, the methods comprising administering to the subject a therapeutically effective amount of one or more enol compounds.

In another aspect, the present disclosure provides methods of treating or preventing chemotherapy-induced neuropathy and ototoxicity in a subject, the methods comprising administering to the subject a therapeutically effective amount of one or more enol compounds selected from the group consisting of NAHA, THA, gavinol, and 2-ACP.

In some embodiments, the methods further comprise administering a chemotherapeutic agent to the subject. In one embodiment, the chemotherapeutic agent is selected from the group consisting of CisPt, CarboPt, and OxaliPt.

In yet another aspect, the present disclosure provides methods of treating cancer in a subject, the methods comprising administering to the subject a chemotherapeutic agent and one or more enol compounds, wherein the subject does not exhibit chemotherapy-induced neuropathy and ototoxicity.

In some embodiments, the one or more enol compounds are selected from the group consisting of NAHA, THA, gavinol, and 2-ACP. In yet another embodiments, the chemotherapeutic agent is selected from the group consisting of CisPt, CarboPt, and OxaliPt.

In some aspects, the present disclosure provides methods of treating cancer in a subject in need thereof, the methods comprising administering to the subject a chemotherapeutic agent selected from the group consisting of CisPt, CarboPt, and OxaliPt and one or more enol compounds selected from the group consisting of NAHA, THA, gavinol, and 2-ACP, wherein the subject does not exhibit chemotherapy-induced neuropathy and ototoxicity.

In certain embodiments, the chemotherapy-induced neuropathy and ototoxicity is caused by CisPt, CarboPt, and OxaliPt.

In one embodiment, the one or more enol compounds is co-administered with the chemotherapeutic agent. In another embodiment, the one or more enol compounds is administered before the chemotherapeutic agent. In yet another embodiment, the one or more enol compounds is administered after a chemotherapeutic agent.

In some embodiments, the one or more enol compounds and the chemotherapeutic agent are administered intraperitoneally, orally, intravenously, intramuscularly, transdermally, intranasally, or through an osmotic mini-pump. In one embodiment, the one or more enol compounds and the chemotherapeutic agent are administered to the subject by different routes.

In certain embodiments, the subject has a testicular cancer, ovarian cancer, cervical cancer, breast cancer, bladder cancer, head and neck cancer, esophageal cancer, lung cancer, mesothelioma, brain tumor, neuroblastoma, non-Hodgkin's lymphoma, endometrial cancer, gastric cancer, Hodgkin's lymphoma, multiple myeloma.

In some embodiments, the neuropathy is sensory neuropathy or neuropathy associated with dorsal root ganglion (DRG) neurons.

In one embodiment, the methods further comprise reducing one or more of paresthesia, tingling, neuropathic pain in the subject, or increasing vibratory sense in the subject.

In some embodiments, the subject is a pediatric subject. In another embodiment, the subject is at least 60 years old.

In some aspects, the present disclosure relates to a composition comprising a therapeutically effective amount of: (a) a chemotherapeutic agent selected from the group consisting of CisPt, CarboPt, and OxaliPt; and (b) an enol compound selected from the group consisting of NAHA, THA, gavinol, and 2-ACP.

In some embodiments, the composition further comprises a pharmaceutically acceptable carrier.

In another embodiment, the composition is a liquid. In yet another embodiment, the composition is encapsulated in a capsule shell.

In one embodiment, the composition comprises about 1 mg/ml of the chemotherapeutic agent.

In another aspect, the present disclosure relates to kits comprising one or more enol compounds or derivatives thereof and a chemotherapeutic agent for use in treating or preventing chemotherapy-induced neuropathy or ototoxicity.

In some embodiments, the kit further comprises instructions for use.

In some embodiments, the one or more enol compounds or derivates thereof are selected from the group consisting of NAHA, THA, gavinol, and 2-ACP.

In yet another embodiment, the chemotherapeutic agent is selected from the group consisting of CisPt, CarboPt, and OxaliPt.

BRIEF DESCRIPTION OF THE DRAWINGS

Figures 1A, 1B, 1C, 1D:
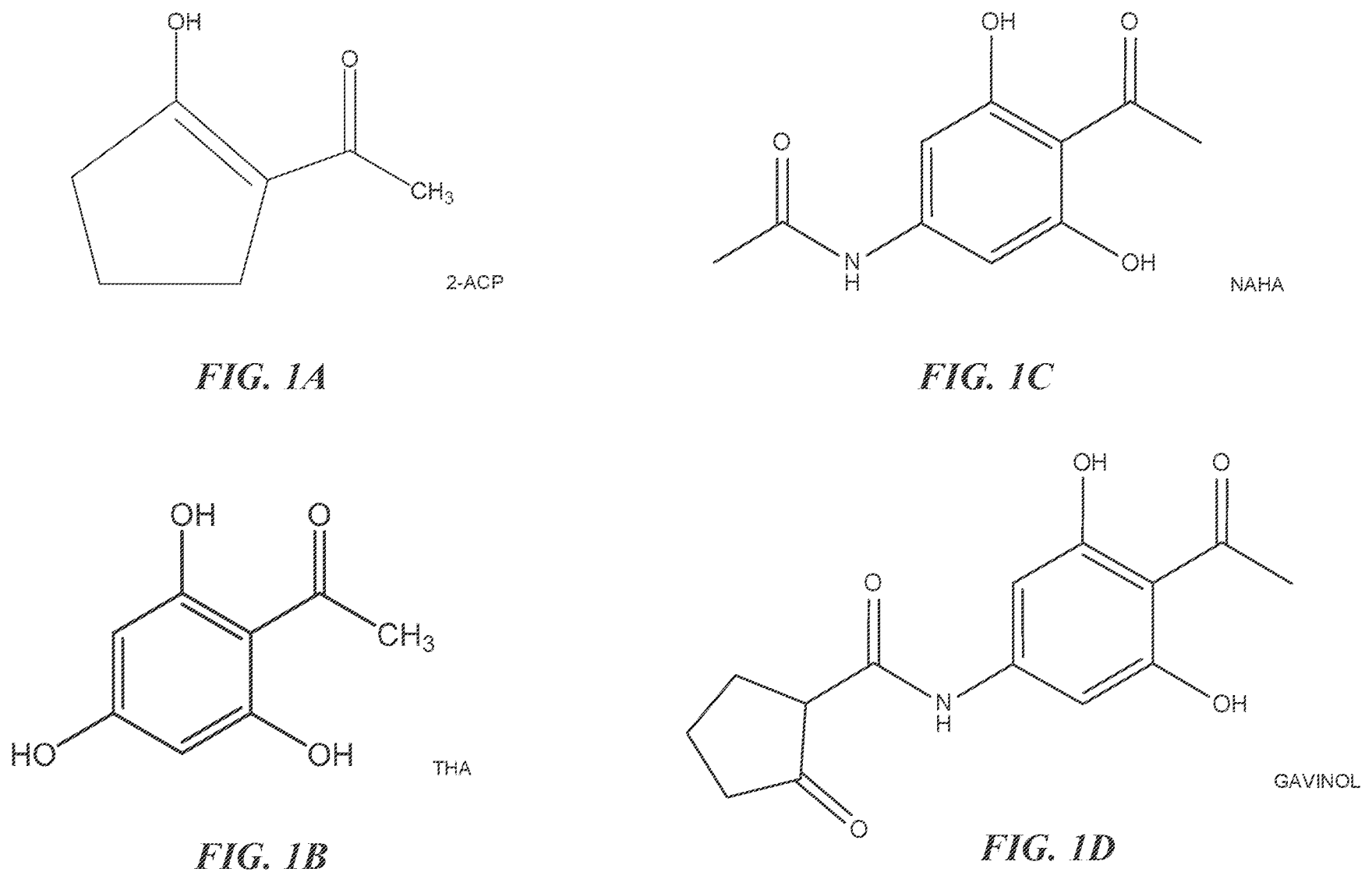

FIG. 1A-1C are depictions of the chemical structures of 2-ACP, THA, NAHA, and gavinol.

DETAILED DESCRIPTION

Figure 2:
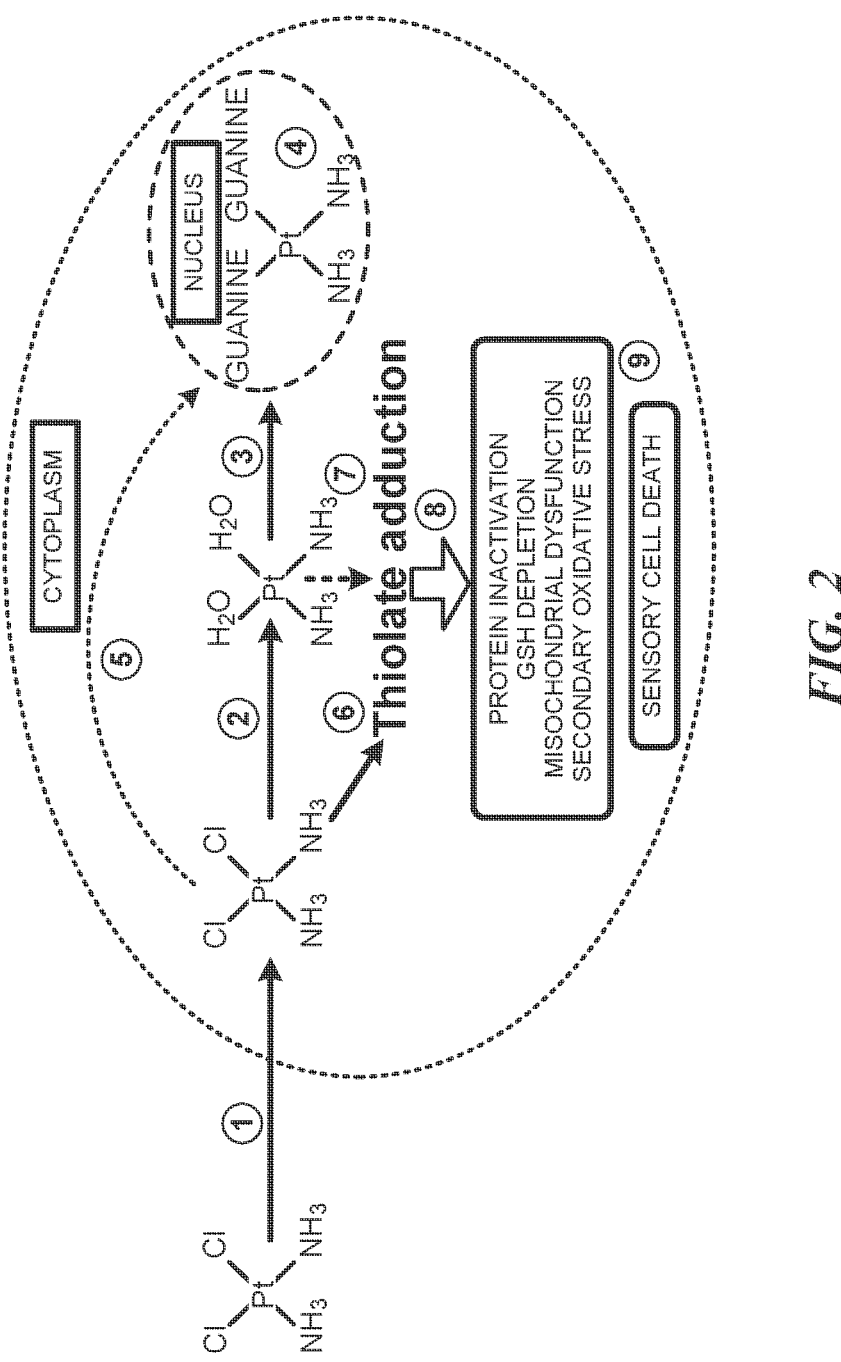
FIG. 2 is a representative schematic depicting the neurotoxicity and chemotherapeutic mechanisms associated with CisPt.

Provided herein are methods, compositions, and compounds for treating or preventing chemotherapy-induced neuropathy and ototoxicity associated with chemotherapeutic agents. These methods, compositions, and compounds utilize one or more enol compounds to treat or prevent chemotherapeutic induced neuropathy and ototoxicity associated with chemotherapy agents without impairing the chemotherapeutic effects of the chemotherapeutic agents.

The development of a neuroprotective drugs that prevent the adverse neurological damage caused by toxic chemotherapeutic agents such as CisPt, CarboPt, and OxaliPt is an unmet need in the field of cancer treatment. The present disclosure relates to the use of nucleophilic enol compounds for reducing neuropathy and ototoxicity associated with chemotherapeutic agents. The results provided herein demonstrate the Pt-containing chemotherapeutic agents, CisPt, CarboPt, and OxaliPt, induce neurotoxicity and chemotherapeutic effects via distinct mechanisms. The discovery of the distinct mechanisms suggest that neurotoxicity can be targeted without interfering with the mechanistic pathway that leads to the chemotherapeutic effects. The results also show that enol compounds react with the Pt from the chemotherapeutic agents to form enol-Pt complexes, which can block the mechanisms that lead to neurotoxicity associated with the chemotherapeutic agents. Lastly, co-administration of the enol compounds and the chemotherapeutic agents showed significant reductions in neurotoxicity without compromising the antitumor efficacy of the chemotherapeutic agents, CisPt, CarboPt, and OxaliPt.

After reading this description it will become apparent to one skilled in the art how to implement the invention in various alternative embodiments and alternative applications. However, all the various embodiments of the present invention will not be described herein. It will be understood that the embodiments presented here are presented by way of example only, and not limitation. As such, this detailed description of various alternative embodiments should not be construed to limit the scope or breadth of the present invention as set forth below.

The detailed description is divided into various sections only for the reader's convenience and disclosure found in any section may be combined with that in another section. Titles or subtitles may be used in the specification for the convenience of a reader, which are not intended to influence the scope of the present disclosure.

Unless the context indicates otherwise, it is specifically intended that the various features of the invention described herein can be used in any combination. Moreover, the disclosure also contemplates that in some embodiments any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Definitions

All numerical designations are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about." It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

The terms "effective" or "sufficient" when used to describe the selection of any components, ranges, dose forms, etc. disclosed herein intend that said component, range, dose form, etc. is suitable for the disclosed purpose.

The term "treating" or "treatment" of a disease or disorder includes at least partially: (1) inhibiting the disease, disorder, or condition, i.e., arresting or reducing the development of the disease, disorder, or condition or its clinical symptoms; or (2) relieving the disease, disorder, or condition, i.e., causing regression of the disease, disorder, or condition or its clinical symptoms.

The term "preventing" or "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician.

The term "pharmaceutically acceptable" in the present context means that the substance in question does not produce unacceptable toxicity to the subject or interaction with other components of the composition.

A "derivative" as used herein, references to any compound derived from a similar compound by a chemical reaction to include any pharmaceutically acceptable salt, metabolites, esters, ethers, hydrates, polymorphs, solvates, complexes, enantiomers or adducts of a compound described herein.

The term "pharmaceutically acceptable excipient" herein means any substance, not itself a therapeutic agent, used as a carrier or vehicle for delivery of a therapeutic agent to a subject or added to a composition to improve its handling or storage properties or to permit or facilitate formation of a unit dose of the composition, and that does not produce unacceptable toxicity or interaction with other components in the composition.

The term "enol" herein means any organic compound that contains a hydroxyl group bonded to a carbon atom having a double bond and that is usually characterized by the grouping $C=C(OH)$.

The phrases "chemotherapeutic agent" herein refers to an agent that reduces, treats, prevents, mitigates, limits, and/or delays cancer or the proliferation of cancerous cells.

The term "chemotherapy" herein refers to treatments or preventive measures using chemotherapeutic agents.

The phrase "platinum-containing drug" or "plantinum-based therapeutic agent" include all compounds, compositions, and formulations which contain a platinum ligated metal. The platinum compositions or platinum compounds of the present invention include, in a non-limiting manner, of the present invention include, in a non-limiting manner, CisPt, OxaliPt, CarboPt, satraplatin, and analogs and derivatives thereof.

Compositions and Compounds

Aspects of the disclosure provide enol compounds and compositions comprising enol compounds for treating chemotherapy-induced neuropathy and/or ototoxicity associated with toxic chemotherapeutic agents.

In some embodiments, the enol compounds are polyphenol compounds or derivatives thereof. In some embodiments, the enol compounds or derivatives thereof have 1, 2, 3, 4, 5, or more enol moieties.

In some embodiments, the polyphenol is selected from the group consisting of 4-N-acetyl-2,6-dihydroxyacetaphenone (NAHA), 2',4',6'-trihydroxyacetophenone (THA), N-(4-acetyl-3,5-dihydroxyphenyl)-2-oxocyclopentane-1-carboxamide (gavinol), and 2-acetylcyclopentanone (2-ACP).

In some embodiments, the enol compounds are administered with a chemotherapeutic agent. In some embodiments, the chemotherapeutic agent is a Pt-based therapeutic agent selected from the group consisting of CisPt, CarboPt, or OxaliPt. In some embodiments, the Pt-based therapeutic agent is satraplatin.

In some embodiments, the chemotherapeutic agent is an electrophile. In some embodiments, the chemotherapeutic agent has an electrophilic index ($\omega$) of about 1 to about 7. For example, in some embodiments, the chemotherapeutic agent has an electrophilic index of about 1, about 2, about 3, about 4, about 5, about 6, or about 7. In some embodiments, the chemotherapeutic agent electrophilic index of about 1 to about 3, about 2 to about 5, about 4 to about 7, about 1 to about 7, about 1 to about 4, about 2 to about 5, or about 3 to about 6.

In some embodiments, the chemotherapeutic agent has properties of a "hard" electrophile. In some embodiments, the chemotherapeutic agent has properties of a "soft" electrophile. In some embodiments, the chemotherapeutic agent has properties of a "hard" and a "soft" electrophile.

In some embodiments, the enol compound is a "soft" nucleophile. In some embodiments, the "soft" nucleophilic properties of the enol compound and the "soft" electrophilic properties of the chemotherapeutic agent form a bond, resulting in an enol-Pt complex. In some embodiments, the enol-Pt complex prevents the chemotherapeutic agent from inducing neuropathy or ototoxicity in the subject.

In some embodiments, the composition comprises a therapeutically effective amount of one or more enol compounds or derivatives thereof. In some embodiments, the composition further comprises a therapeutically effective amount of one or more chemotherapeutic agent.

In some embodiments, the composition comprises a therapeutically effect amount: (a) of a chemotherapeutic agent and (b) an enol compound or derivative thereof. In some embodiments, the therapeutically effective amount of the chemotherapeutic agent is an amount sufficient to treat and/or prevent cancer. In another embodiment, the therapeutically effective amount of the enol compound or derivative thereof is an amount sufficient to treat and/or prevent chemotherapy-induced neuropathy and/or ototoxicity.

In another embodiment, compositions comprise one or more pharmaceutically acceptable excipients. By way of example only, a pharmaceutically acceptable excipient may comprise one or more of: antioxidants, surfactants, preservatives, flavoring agents, co-solvents, viscosity aids, suspension aids, and lipophilic phases.

In some embodiments, the composition is a liquid composition. In some embodiments, the composition comprises about 0.1 mg/ml, about 0.15 mg/ml, about 0.2 mg/ml, about 0.25 mg/ml, about 0.30 mg/ml, about 0.35 mg/ml, about 0.40 mg/ml, about 0.45 mg/ml, about 0.5 mg/ml, about 0.55 mg/ml, about 0.60 mg/ml, about 0.65 mg/ml, about 0.70 mg/ml, about 0.75 mg/ml, about 0.80 mg/ml, about 0.85 mg/ml, about 0.90 mg/ml, about 0.95 mg/ml, or about 1 mg/ml of a Pt-containing drug. In some embodiments, the compositions comprise about 0.1 mg/ml to about 1 mg/m I, about 0.2 mg/ml to about 0.5 mg/ml, about 0.4 mg/ml to about 0.6 mg/ml, about 0.4 mg/ml to about 1 mg/ml, about 0.70 mg/ml to about 0.95 mg/ml, or about 0.25 mg/ml to about 0.90 mg/ml. In some embodiments, the Pt-containing drug is one or more of CisPt, CarboPt, or OxaliPt.

In some embodiments, the compositions comprise CisPt, CarboPt, or OxaliPt and NAHA. In some embodiments, the compositions comprise CisPt, CarboPt, or OxaliPt and THA. In another embodiment, the compositions comprise CisPt, CarboPt, or OxaliPt and gavinol. In yet another embodiment, the compositions comprise CisPt, CarboPt, or OxaliPt and 2-ACP.

In some embodiments, the enol compounds of the compositions are provided as a tautomer thereof; or a geometric or optical isomer thereof; or racemate thereof; or a pharmaceutically acceptable salt thereof. Pharmaceutically acceptable salts that can be used include non-toxic salts derived from inorganic or organic acids, including, for example, the following acid salts: acetate, adipate, alginate, aspartate, benzoate, benzenesulfonate, bisulfate, butyrate, citrate, camphorate, cam phorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

In some embodiments, enol compounds are formulated for administration to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration.

In some embodiments, the pharmaceutical compositions can be formulated for administration by any method known in the art, including but not limited to, oral administration, parenteral administration, intraperitoneal administration, intravenous administration, intramuscular administration, transdermal administration, intranasal administration, and administration through an osmotic mini-pump.

In some embodiments, the composition is formulated for oral administration. In some embodiments, the composition formulated for oral administration is encapsulated in a capsule shell. In some embodiments, the capsule shell has an enteric coating or wax coating. In some embodiments, enteric or wax coating can be stable at the acidic pH found in the stomach but can break down in the alkaline environment of the small intestine. In some embodiments, the enteric coatings comprise fatty acids or plant fibers.

In some embodiments, enol compounds or the compositions comprising enol compounds are formulated for topical administration. For example, the enol compounds or the compositions comprising enol compounds can be formulated for application to the skin as a cream or as sustained release formulations or patches.

In some embodiments, the enol compound or a composition comprising the enol compound are formulated for administration to the subject at the same time as the chemotherapeutic agent. In some embodiments, the enol compound or composition comprising the enol compound and the chemotherapeutic agent are formulated for simultaneous administration.

In some embodiments, the enol compound or a composition comprising the enol compound and the chemotherapeutic agent are formulated for administration in the same formulation. In some embodiments, the composition comprises both the enol compound and the chemotherapeutic agent.

In some embodiments, the enol compound or a composition comprising the enol compound are formulated for administration to the subject prior to administration of the chemotherapeutic agent. In yet another embodiment, the enol compound or a composition comprising the enol compound is formulated for administration to the subject after administration of the chemotherapeutic agent.

Methods

Aspects of the disclosure provide methods for treating or preventing chemotherapy-induced neuropathy and/or ototoxicity using enol compounds and compositions comprising enol compounds.

In some embodiments, the present disclosure provides methods of treating and/or preventing chemotherapy-induced neuropathy and/or ototoxicity in a subject, the method comprising administering to the subject a therapeutically effective amount of one or more enol compounds.

In yet another embodiment, the present disclosure provides methods of treating cancer in a subject, the methods comprising administering to the subject a chemotherapeutic agent and one or more enol compounds, wherein the subject does not exhibit chemotherapy-induced neuropathy and/or ototoxicity.

In some embodiments, the present disclosure provides methods of treating and/or preventing chemotherapy-induced neuropathy and/or ototoxicity in a subject, the methods comprising administering to the subject a therapeutically effective amount of one or more enol compounds selected from the group consisting of NAHA, THA, gavinol, and 2-ACP.

In another embodiment, the present disclosure provides methods of treating cancer in a subject, the methods comprising administering to the subject a chemotherapeutic agent selected from the group consisting of CisPt, CarboPt, and OxaliPt and one or more enol-based compounds selected from the group consisting of NAHA, THA, gavinol, and 2-ACP, wherein the subject does not exhibit chemotherapy-induced neuropathy and/or ototoxicity.

In some embodiments, the methods include treating or preventing large-fiber peripheral neuropathy, small fiber peripheral neuropathy, peripheral sensory neuropathy, peripheral neuropathy motion, and/or motion sensory neuropathy associated with the chemotherapeutic agents. In some embodiments, the neuropathy is sensory neuropathy.

In some embodiments, the neuropathy is associated with sensory dorsal root ganglion (DRG) neurons.

In some embodiments, the methods reduce one or more of paresthesia, tingling, neuropathic pain in the subject caused by the chemotherapeutic agent. In another embodiment, the methods increase vibratory sense in the subject caused by the chemotherapeutic agent.

In some embodiments, the subject has been previously identified as having cancer. Non-limiting examples of cancer include testicular cancer, ovarian cancer, cervical cancer, breast cancer, bladder cancer, head and neck cancer, esophageal cancer, lung cancer, mesothelioma, brain tumor, neuroblastoma, non-Hodgkin's lymphoma, endometrial cancer, gastric cancer, Hodgkin's lymphoma, multiple myeloma. In some embodiments, the lung cancer is a non-small cell lung cancer.

In some embodiments, the methods include treating chemotherapy-induced neuropathy and/or ototoxicity associated with CisPt, CarboPt, and/or OxaliPt in a subject, comprising administering to the subject one or more enol compounds selected from the group consisting of NAHA, THA, gavinol, or 2-ACP. In some embodiments, the subject is administered a composition comprising the chemotherapeutic agent and the enol compound. That is, in some embodiments, the subject is administered the chemotherapeutic agent and the enol compound simultaneously. In an alternative embodiment, the subject is administered the enol compound prior to administration of the chemotherapeutic agent. In yet another embodiment, the subject is administered the chemotherapeutic agent prior to being administered the enol compound.

In some embodiments, the methods comprise treating or preventing chemotherapy-induced neuropathy or ototoxicity in a subject by administering to the subject: (a) a composition comprising the chemotherapeutic agent and (b) the enol compound or a composition comprising the enol compound. In some embodiments, administering the chemotherapeutic agent prior to the enol compound or composition comprising the enol compound delays the onset of chemotherapy-induced neuropathy and/or ototoxicity.

In another embodiment, the methods comprise treating or preventing chemotherapy-induced neuropathy and/or ototoxicity in subject by administering to the subject: (a) the enol compound or a composition comprising the enol compound and (b) a composition comprising the chemotherapeutic agent. In some embodiments, administering the enol compound or composition comprising the enol compound prior to the chemotherapeutic agent delays the onset of chemotherapy-induced neuropathy and/or ototoxicity.

In some embodiments, the methods comprise treating or preventing chemotherapy-induced neuropathy and/or ototoxicity in subject by administering to the subject a composition comprising an enol compound and a chemotherapeutic agent. In some embodiments, administering the enol compound or composition comprising the enol compound with the chemotherapeutic agent delays the onset of chemotherapy-induced neuropathy and/or ototoxicity.

In some embodiments, the methods comprise treating or preventing chemotherapy-induced neuropathy and/or ototoxicity in a subject by administering an enol compound and CisPt, CarboPt, and/or OxaliPt, wherein the enol compound forms an enol-Pt complex that prevents the Pt compound from inducing neuropathy or ototoxicity.

In some embodiments, the methods comprise treating or preventing chemotherapy-induced neuropathy and/or ototoxicity in a subject by administering an enol compound and CisPt, CarboPt, and/or OxaliPt, wherein the enol compound does not interfere with the chemotherapeutic effects of CisPt, CarboPt, and/or OxaliPt.

In some embodiments, the methods comprise treating or preventing cancer in a subject by administered an enol based compound and a chemotherapeutic agent, wherein the enol based compound serves as a chemoprotective agent and increases the chemotherapeutic index of the chemotherapeutic agent by allowing increases in dose, frequency, and duration of the chemotherapeutic agent administration.

In some embodiments, the methods comprise administering to the subject the chemotherapeutic agent, enol compound, and/or composition comprising the enol compound once daily, at least about once every week, at least about once every two weeks, at least about once every three weeks, at least about once every two days, at least about once every three days, at least about once every four days, at least about once every five days, or at least about once every seven days.

In certain embodiments, the methods comprise administering the enol compound and/or chemotherapeutic agent at a specific time course determined in advance. For example, the enol compound and/or chemotherapeutic agent may be administered for a time course of 2 weeks, 4 weeks, 6 weeks, 8 weeks, 12 weeks, 16 weeks, 20 weeks, 24 weeks, 36 weeks, 48 weeks, 1 year, 18 months, 2 years, or more than 2 years. In other embodiments, the one or more enol compound and/or chemotherapeutic agent may be administered indefinitely, or until a specific therapeutic benchmark is reached. For example, the one or more enol compound and/or chemotherapeutic agent may be administered until one or more symptoms of cancer, neuropathy, and/or ototoxicity is reduced, treated, and/or prevented.

In certain embodiments, both the administration frequency and the dosage of the enol compound and/or chemotherapeutic agent may be adjusted over the course of treatment.

In some embodiments, the methods comprise administering the one or more enol compounds and the chemotherapeutic agent to the subject intravenously. In another embodiment, the methods comprise administering the one or more enol compounds and the chemotherapeutic agent to the subject orally. In some embodiments, the methods comprise administering the one or more enol compounds and the chemotherapeutic agent to the subject intraperitoneally. In some embodiments, the methods comprise administering the one or more enol compounds and the chemotherapeutic agent to the subject intramuscularly. In yet another embodiment, the methods comprise administering the one or more enol compounds and the chemotherapeutic agent to the subject transdermally. In another embodiment, the methods comprise administering the one or more enol compounds and the chemotherapeutic agent to the subject intranasally. In some embodiments, the methods comprise administering the one or more enol compounds and the chemotherapeutic agent to the subject through an osmotic mini-pump.

In some embodiments, the methods comprise administering the one or more enol compounds and the chemotherapeutic agent to the subject to the subject by different routes. For example, in some embodiments, the chemotherapeutic agent is administered to the subject intravenously and the more or more enol compounds is administered to the subject orally or intramuscularly.

In some embodiments, the methods comprise reducing ototoxicity associated with the chemotherapeutic agent in a subject. In some embodiments, the ototoxicity associated with the chemotherapeutic agent in a subject is an outer hair cell ototoxicity.

In some embodiments, the methods further comprise reducing the following chemotherapeutic toxicities: nephrotoxicity, allergic or hypersensitivity reactions, hepatic toxicity, and/or myelosuppression.

In some embodiments, the subject is a pediatric patient. For example, in some embodiments, the subject is about 1, about 2, about 3, about 4, about 5, about 6, about 7, about 8, about 9, about 10, about 11, about 12, about 13, about 14, about 15, about 16, about 17, or about 18 years old. In some embodiments, the subject is about 1 to about 15, about 1 to about 5, about 3 to about 10, about 9 to about 18, about 1 to about 18, about 5 to about 10, or about 1 to about 15 years old.

In some embodiments, the subject is 60 years old or more. For example, in some embodiments, the subject is about 60, about 65, about 70, about 75, about 80, or greater. In some embodiments, the subject is about 60 to about 80, about 60 to about 70, about 70 to about 80, about 65 to about 75, or about 65 to about 80 years old.

Kits

The, compounds, compositions, and formulations of the invention, alone or in combination with one or more chemotherapeutic agents, and instructions for their use, may be included in a form of kits.

In some embodiments, the kit comprises: (a) one or more enol compounds or a composition comprising one or enol compounds; (b) one or more chemotherapeutic agents or a composition comprising one or more chemotherapeutic agents; and (c) instructions for use.

In some embodiments, the kit comprises one or more enol compounds selected from the group consisting of NAHA, THA, gavinol, or 2-ACP. In some embodiments, the kit further comprises one or more chemotherapeutic agents selected from the group consisting of CisPt, CarboPt, and OxaliPt, In certain embodiments, the kit is for use in treating or preventing chemotherapeutic neuropathy and/or ototoxicity. In some embodiments, the kit is for use in treating or preventing cancer without causing chemotherapeutic induced neuropathy and/or ototoxicity.

EXAMPLES

The foregoing and the following working examples are merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein.

Cisplatin (CisPt) and other platinum (Pt)-containing drugs such as carboplatin (CarboPt) and oxaliplatin (OxaliPt) are a class of anticancer agents used to treat solid tumors. This class of anticancer agents kill cancer cells by damaging or inhibiting DNA synthesis. (1-3). However, these Pt-containing drugs are also highly toxic to the peripheral nervous system. Thus, the efficacy of Pt-containing drugs is comprised by dose-limiting neurotoxicity. (1,2,4-10). Accordingly, there is a need to develop therapies that reduce neurological damage associated with the administration of the Pt-containing drugs without reducing chemotherapeutic effects.

The objectives of the following study were to: (1) investigate the electronic structure of Pt-containing drugs to determine how the drugs induce chemotherapeutic effects and neurotoxicity; (2) evaluate the ability of enol compounds to form complexes with Pt-containing drugs to prevent neurotoxicity; (3) determine the efficacy enol compounds to reduce neurotoxicity; and (4) examine whether the enol compounds disrupt the chemotherapeutic effects of the Pt-containing drugs.

Significantly, the results from this study demonstrate that the mechanisms that induce neurotoxicity and chemotherapy upon the administration of Pt-containing drugs are different and can therefore, be targeted separately. Furthermore, the initial results indicated that enol compounds and the Pt-containing drugs, form enol-Pt complexes that block the mechanisms that govern neurotoxicity of the Pt-containing drugs. It was then determined that enol compounds, when co-administered with Pt-containing drugs, reduce neurotoxicity without impairing the antitumor efficacy of the Pt-containing drugs.

The Electronic Character of Platinum-Containing Drugs

Initial efforts focused on understanding the electronic structure of the Pt-containing drugs in order to determine whether the co-administration of enol compounds would interfere with the chemotherapeutic activity of the Pt-containing drugs and whether the respective mechanisms of neurotoxicity (soft-soft reactions) and chemotherapy (hard-hard reactions) are separable and can therefore, be affected independently.

To understand the electronic structure of CisPt, a model for CisPt-induced neurotoxicity was developed based on the electronic structure of the Pt ion of the complex as shown in FIG. 2. FIG. 2 shows that while CisPt cellular entry at step (1) is unknown (e.g., passive diffusion, CTR1 or OCT1-3), entry is associated with "aquation" as shown at step (2) where the chlorine (Cl) ligands of CisPt are displaced by water molecules. The CisPt water ligated complex then enters the nucleus of the cell at step (3). The process of exchanging the CI for water molecules hardens the soft electrophilic character of CisPt and, as a result, this harder molecule reacts more favorably with the hard guanine target as show in in step (4). However, the non-aquated soft CisPt at step (5) can also react with guanine, although this soft-hard interaction is not kinetically favored. The chlorinated soft CisPt electrophile at step (6) can form adducts with anionic sulfur groups on GSH and proteins (i.e., thiolate adduction). Lastly, the aquated CisPt at step (7) can also deplete GSH content, although this soft-hard reaction is not favored. The soft-soft reaction of the thiolate with CisPt causes at step (8) protein inactivation, GSH depletion, mitochondrial dysfunction and secondary oxidative stress. This toxic cascade results in sensory neuropathy and/or ototoxicity as shown at step (9). Accordingly, FIG. 2 depicts the proposed mechanistic pathway for CisPt induced chemotherapy and neurotoxicity.

The proposed mechanism depicted in FIG. 2 can be related back to the chemical structure of the Pt-containing drugs. Square planar Pt complexes (e.g., CisPt) are electrophiles that can cause toxicity by forming adducts with nucleophilic residues of biological macromolecules. (2,11-13). However, electrophiles do not arbitrarily react with nucleophiles, rather these covalent interactions are relatively selective, as predicted by the hard and soft acids and bases (HSAB) theory of Pearson (14-16). Based on relative polarizability (i.e., electron mobility), electrophiles and nucleophiles are classified as being either "soft" (i.e., polarizable) or "hard" (i.e., non-polarizable).

In accordance with HSAB principles, toxic electrophiles will react preferentially with nucleophilic biological targets of comparable softness or hardness. The designation of "hard" or "soft" is quantifiable based on corresponding inherent electronic characteristics that can be computed from the energies of the respective frontier molecular orbitals; i.e., the highest occupied molecular orbital ($E_{HoMo}$) and the lowest unoccupied molecular orbital ($E_{Lumo}$). These energies have been used to develop parameters that define the electrophilicity ($\omega$) and nucleophilicity ($\omega-$) of chemical species. CisPt is considered to be a reactive soft electrophile since electrons in the frontier molecular orbitals are polarizable as reflected in the respective softness ($\sigma$) and electrophilicity ($\omega$) values.

The electrophilic parameters for CisPt and other Pt-containing drugs to include aqua-CisPt, OxaliPt, and CarboPt were computed as shown in Table 1. As a point of comparison, the electrophilic parameters of two highly reactive soft electrophiles, N-acetyl-p-benzoquinone imine (NAPQI) and acrolein were also computed. To determine the electrophilic parameters, ground state equilibrium geometries were calculated for each structure with density functional theory (DFT) using B3LYP-6.3G* in water from initial 6-31G* geometries. LUMO and HOMO energies were generated exclusively from corresponding s-cis conformation for each complex and were used to calculate hardness ($\eta$) and softness ($\sigma$), and electrophilic index ($\omega$).

As shown in Table 1, the HSAB profile of CisPt ($\eta=2.5$; $\sigma=400$; $\omega=3.43$) is similar to that of both the reactive soft electrophiles, NAPQI ($\eta=1.9$; $\sigma=520$; $\omega=6.83$) and acrolein ($\eta=2.7$; $\sigma=370$; $\omega=3.82$). It is the soft electrophilic character of CisPt, NAPQI, and acrolein that is contemplated to be the feature that induces neurotoxicity by forming adducts with soft nucleophilic sites on biological macromolecules (soft-soft reactions).

TABLE 1

Electrophile HSAB Parameters

| Compound | $\eta$ (ev) | $\sigma(\times10^{-3}\,ev^{-1})$ | $\omega$ (ev) |
|---|---|---|---|
| CisPt | 2.5 | 400 | 3.43 |
| Aqua-CisPt | 2.7 | 370 | 4.38 |
| OxaliPt | 2.8 | 360 | 2.44 |
| CarboPt | 5.0 | 200 | 1.29 |
| NAPQI | 1.9 | 520 | 6.83 |
| Acrolein | 2.7 | 370 | 3.82 |

However, the computations from this study indicate that the Pt orbitals of CisPt also include non-polarizable electron densities that denote hard electrophilic character (Table 2). It is contemplated that the hard electrophilic character of CisPt is the feature that induces chemotherapeutic effects by forming adducts with the hard nucleophilic sites on biological macromolecules (hard-hard reactions).

The nucleophilic index (co-) indicates the propensity to form a covalent bond between a reacting electrophile with a selected nucleophile. To evaluate the Pt-containing drugs preference for forming bonds with compounds having features similar to DNA (hard-hard reactions) vs. enol compounds (soft-soft interactions), the nucleophilic index was calculated for the nucleic acid, guanine (hard nucleophile) and the enol compounds, NAHA and gavinol (soft nucleophiles) as shown in Table 2.

TABLE 2

Nucleophilic Index ($\omega-$; ev)

| Electrophiles | Guanine (hard) | NAHA (soft) | Gavinol (soft) |
|---|---|---|---|
| Cisplatin | 0.071 | 0.220 | 0.359 |
| Aqua-CisPt | 0.170 | 0.343 | 0.501 |
| OxaliPt | 0.024 | 0.121 | 0.220 |
| CarboPt | 0.010 | 0.044 | 0.082 |
| NAPQI | 0.322 | 0.676 | 0.960 |
| Acrolein | 0.096 | 0.243 | 0.370 |

Based on the HSAB profile of each of the Pt-containing compounds, the hard electrophilic character of the Pt-containing compounds will preferentially react with the hard nucleophiles such as the oxygen and nitrogen atoms of DNA nucleobases (i.e., guanine). In contrast, the enol compounds, soft carbon nucleophiles, will react slowly with the hard electrophilic character of CisPt. Significantly, this suggests that enol compound will not interfere with the hard-hard chemotherapeutic activity of CisPt with DNA-based nucleophiles (FIG. 2).

Since Pt ions exhibit both hard and soft electrophilic features and, as a reactive soft electrophile, it is contemplated that Pt causes cell toxicity by reacting with soft nucleophiles that are involved in critical biological activity; e.g., enzyme activity, mitochondrial function (FIG. 2, step 8). However, because CisPt also exhibits hard electrophilic character that mediates covalent reactions with hard nucleophilic sites on DNA; e.g., nitrogen, oxygen residues, it is contemplated that this hard-hard interaction mediates DNA cross-linking which prevents transcription and thereby causes cancer cell death (FIG. 2, step 3). These observations indicate that the respective mechanisms of neurotoxicity (soft-soft reactions) and chemotherapy (hard-hard reactions) are separable and can therefore be affected independently.

Accordingly, this research provides a rational basis for predicting that multifunctional enolate-forming compounds might be protective in experimental neurotoxicity. Based on the stated mechanism of cytoprotection (soft-soft reaction), enol derivatives can directly intercept Pt and thereby prevent initiation of the injury cascade displayed in FIG. 2.

Having determined, computationally, that enol compounds might not interfere with the chemotherapeutic activity (hard-hard reaction) of CisPt and that the mechanisms for neurotoxicity and chemotherapy are separable, the next stage of this study focused on evaluating, experimentally, the ability of enol compounds to reduce the neurotoxicity of CisPt, CarboPt, and OxaliPt.

Characterization of the Enolate-Cisplatin Complexes

Based on the preceding evidence, the working premise is that the soft nucleophilic enolate moiety forms stable complexes with the soft electrophilic attributes of the Pt ion and these complexes, prevent soft electrophile-mediated cytotoxicity. To more fully explore this possibility, the enol compounds were incubated with CisPt to determine if enol-Pt complexes form.

The enol compounds 4-N-acetyl-2,6-dihydroxyacetaphenone (NAHA), 2',4',6%-trihydroxyacetophenone (THA), and N-(4-acetyl-3,5-dihydroxyphenyl)-2-oxocyclopentane-1-carboxamide (gavinol) were incubated for 2 hours in chemico with CisPt and resulting enol-Pt complexes were identified using mass spectrometry (MS). A flow injection analysis was performed with an HP1100 HPLC using a mobile phase consisting of 50% acetonitrile/water containing 0.1% formic acid and flowing at 75

μL/min. Samples, 40 μL, were diluted with 140 μL of deionized $H_2O$. After injecting 20 μL of the diluted samples, the effluent was connected to an Orbitrap Velos mass spectrometer using positive electrospray ionization and scanning from m/z 110 to 1600. Scans were averaged over the top half of the elution peak and background subtracted to provide the mass spectra of each enol-Pt complex.

Results showed that CisPt and, for example, NAHA were observed separately at 306.01 and 210.07. Tandem MS using a wide isolation window revealed complexes composed of PtCl/NAHA (m/z 444) and Pt/Cl/NH3/NAHA (m/z 463). MS analyses of the other listed enol compounds indicated similar complexation. These data suggest that enol ligands can form varied organometallic adducts with CisPt and therefore, support the mechanistic hypothesis that the enol compounds prevent toxicity by forming complexes with the Pt-containing compounds.

Enolate-Forming Compounds to Prevent Toxicity

The preceding spectrometric study provided direct evidence that enol compounds can form complexes with Pt. However, the toxicity of the resulting enol-Pt complexes has not been determined. Accordingly, the next phase of the study was to evaluate the toxicity of the resulting enol-Pt complexes.

Figure 3A:
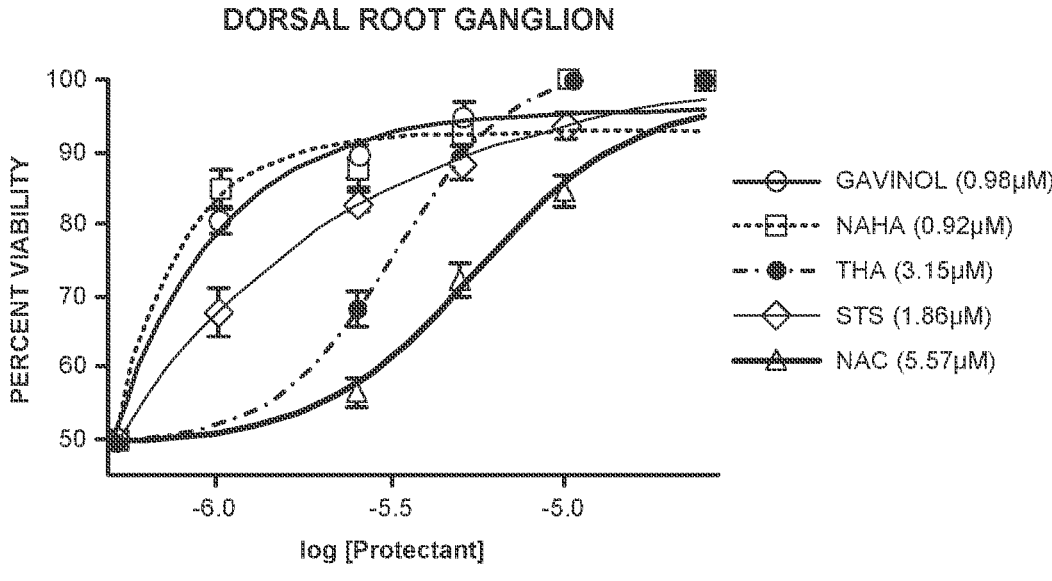
FIG. 3A-3B are representative graphs depicting the ability of enol and thiol compounds to prevent CisPt induced cytotoxicity in neonatal DRG cells and hepatocyte cells, respectively.
Figure 3B:
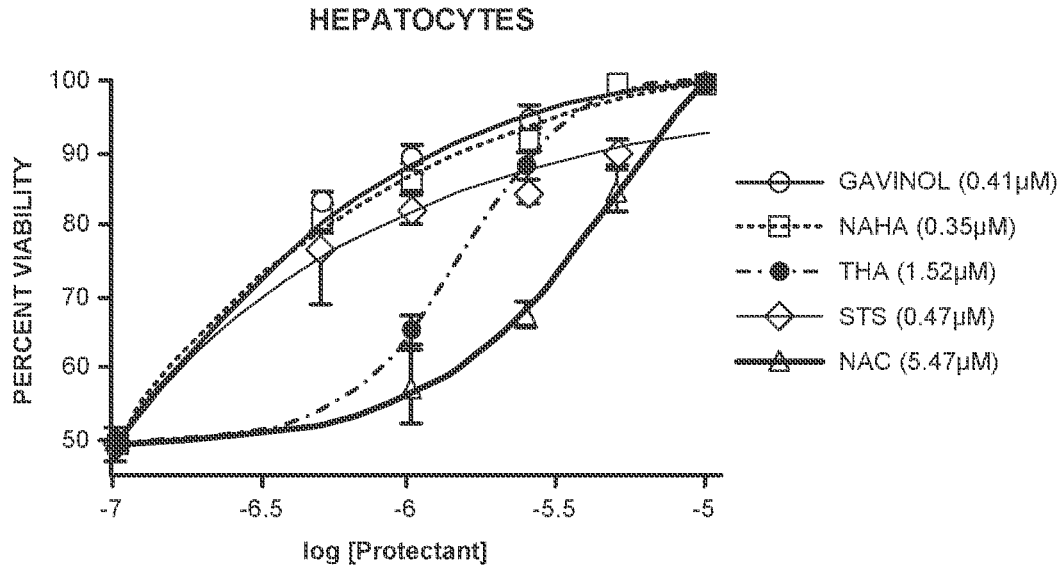

The enol compounds investigated in this study were gavinol, NAHA, and THA and as a point of comparison, the protective properties of thiol-based compounds, N-acetyl-L-cysteine (NAC) and sodium thiosulfate (STS), were also investigated. To determine the ability of enol compounds to reduce neurotoxicity, the dose dependent effects of CisPt on the viability of neonatal rat DRG cells (FIG. 3A) and freshly isolated mouse hepatocytes (FIG. 3B) in the presence or absence of the protectant were measured. The results indicated that CisPt caused concentration-dependent toxicity in both cell models. However, co-administration of CisPt with gavinol, NAHA, and THA provided substantial cryoprotection as evidenced by the relatively small $IC_{75S}$ concentrations. In contrast, thiol-based compounds, NAC and STS, provided only modest protection.

Figure 4A:
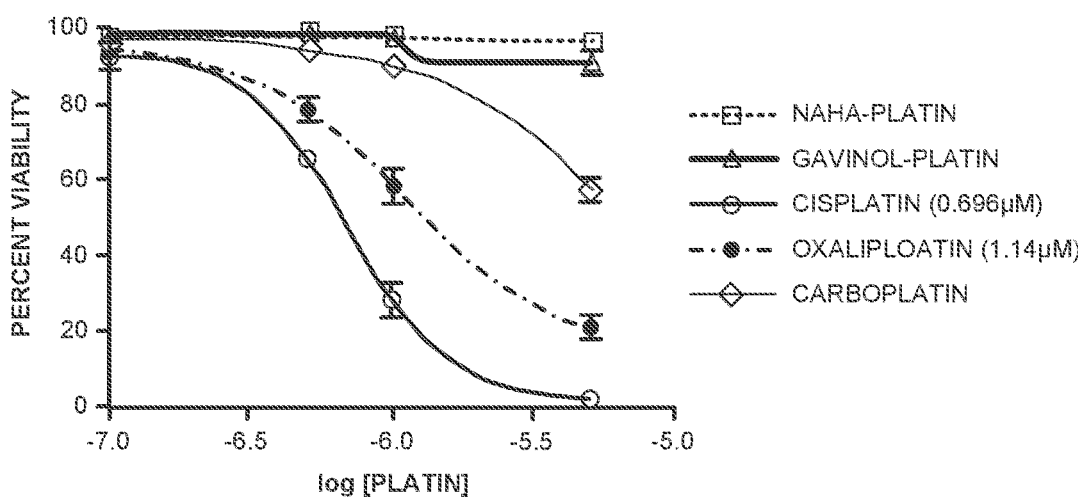
FIG. 4A-4B are representative graphs depicting the ability of enol-Pt complexes to prevent CisPt induced cytotoxicity in neonatal DRG cells and hepatocyte cells, respectively.
Figure 4B:
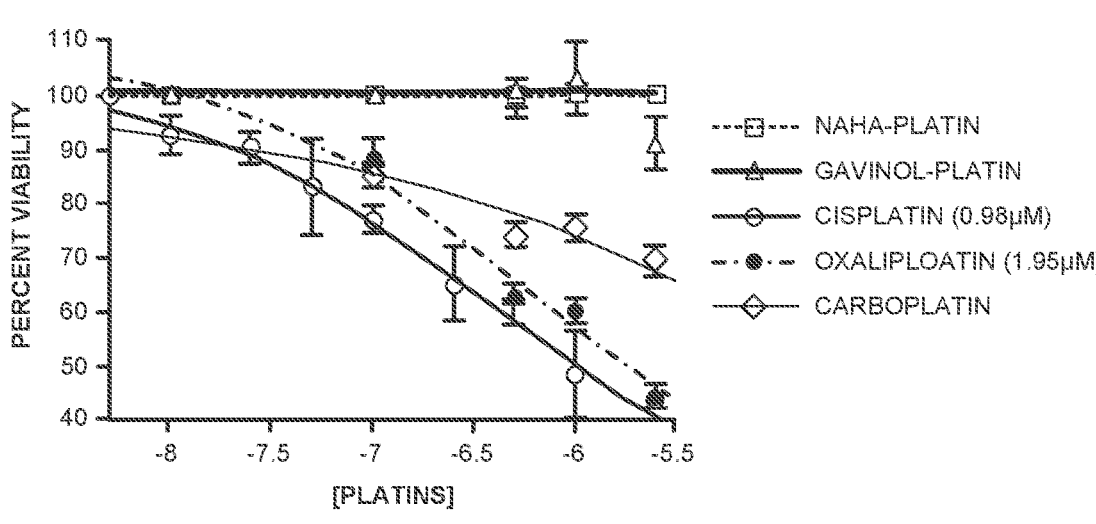

The preceding data are consistent with the possibility that enol compounds form non-toxic complexes with CisPt and corresponding Pt-containing drugs. To test this hypothesis, enol compounds were pre-incubated with CisPt, OxaliPt, and CarboPt for 30 mins to form enol-Pt complexes. DRG cells and isolated mouse hepatocytes were then exposed to enol-Pt complexes for 4 hours and the respective changes in lethality were determined. As shown in FIGS. 4A and 4B, exposure to the enol-Pt complexes (e.g., NAHA-Pt; gavinol-Pt) did not cause hepatocyte or DRG cytotoxicity over a broad concentration range, respectively. In contrast, exposure of normal (i.e., non-cancer) cells to CisPt, OxaliPt, and CarboPt, without the enol compounds, caused substantial concentration-dependent DRG and hepatocyte lethality. CarboPt produced intermediate cytotoxicity relative to that caused by CisPt or OxaliPt.

The decreased cytotoxicity of CarboPt could be due to the fact that CarboPt is a very hard drug with low electrophilicity. The limited electrophilic reactivity is likely related to ligand retention strength. That is, CisPt carries 2 chlorines and 2 amine groups, whereas the CarboPt leaving group is a cyclobutane-1,1-dicarboxylic acid. The CisPt chlorines are excellent leaving groups, whereas the ligand retention strength for cyclobutane is very high which will, in turn, lower the effective electrophilic reactivity. The partial toxicity of CarboPt is also consistent with fact that this congener is a modestly reactive soft electrophile.

Accordingly, these results suggest that enol compounds prevent toxicity by forming non-toxic complexes with Pt-based analogues and do not impart any adverse toxic effects.

Influence of Enolate-Forming Compounds on CisPt-Induced Cancer Cell Lethality

Having determined that the enol-Pt complexes reduce the neurotoxicity associated with the administration of Pt-containing drugs such as CisPt, OxaliPt, and CarboPt, the next steps of this study were to determine whether the enol-Pt complexes disrupt the chemotherapeutic effects of the Pt-containing drugs.

Figure 5A:
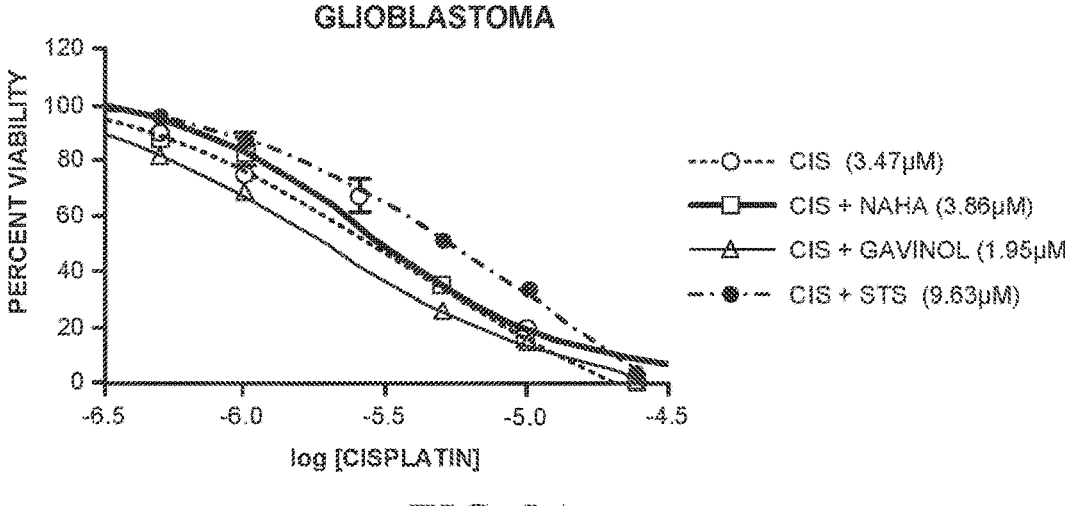
FIG. 5A-5C are representative graphs depicting the ability of enol compounds to prevent cytotoxicity without minimizing the chemotherapeutic effects of CisPt, CarboPt, and OxaliPt in neonatal DRG cells and hepatocyte cells, respectively.
Figure 5B:
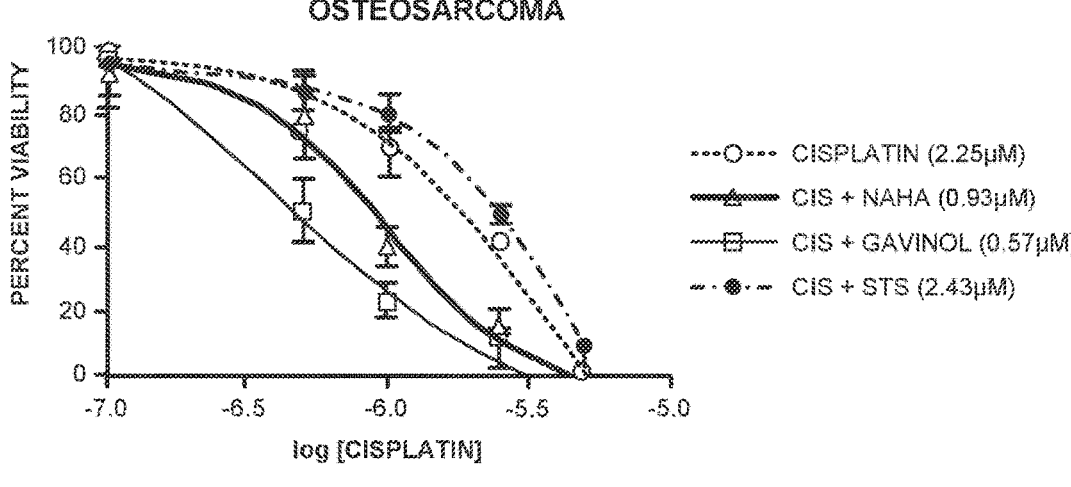
Figure 5C:
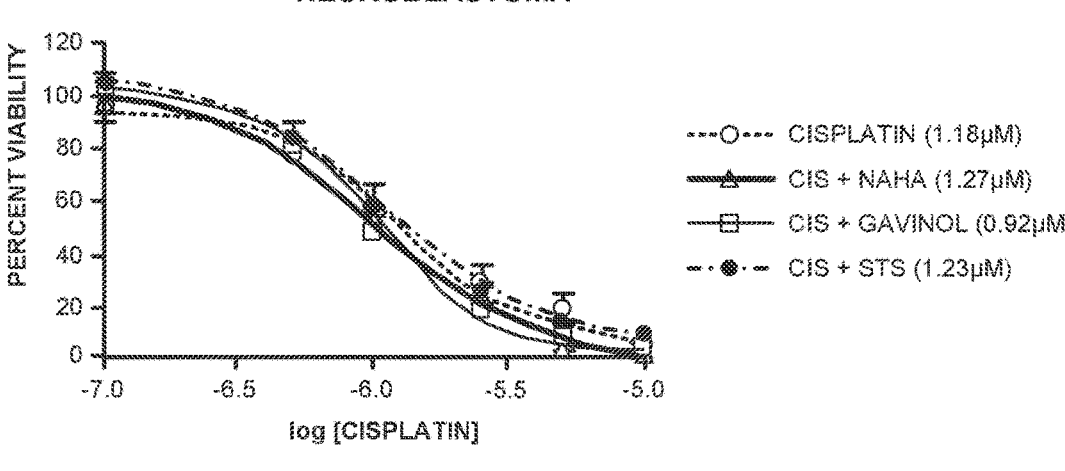

To test the possibility that putative enol neuroprotectants might reduce or otherwise modify CisPt chemotherapeutic efficacy, different cancer cell lines to include glioblastoma (U87 MG), osteosarcoma (HOS) and neuroblastoma (SH-SY5) were co-incubated with graded concentrations of CisPt in the presence or absence of an enol compound (e.g., NAHA or Gavinol) or thiol nucleophiles (e.g., NAC or STS). The results indicated that enol compounds do not alter the ability of CisPt to kill neuroblastoma (FIG. 5A) and glioblastoma (FIG. 5B) cells as evidenced by the quantitative similarity of respective $IC_{75S}$. However, in osteosarcoma cells (FIG. 5C), CisPt complexes of gavinol or NAHA significantly lowered the respective $IC_{75S}$, indicating a potentiation of cancer cell death. Parallel studies showed that a selected thiol-protectant, STS, also did not modify CisPt-induced cancer cell toxicity (FIG. 5A-5C).

Figure 6A:
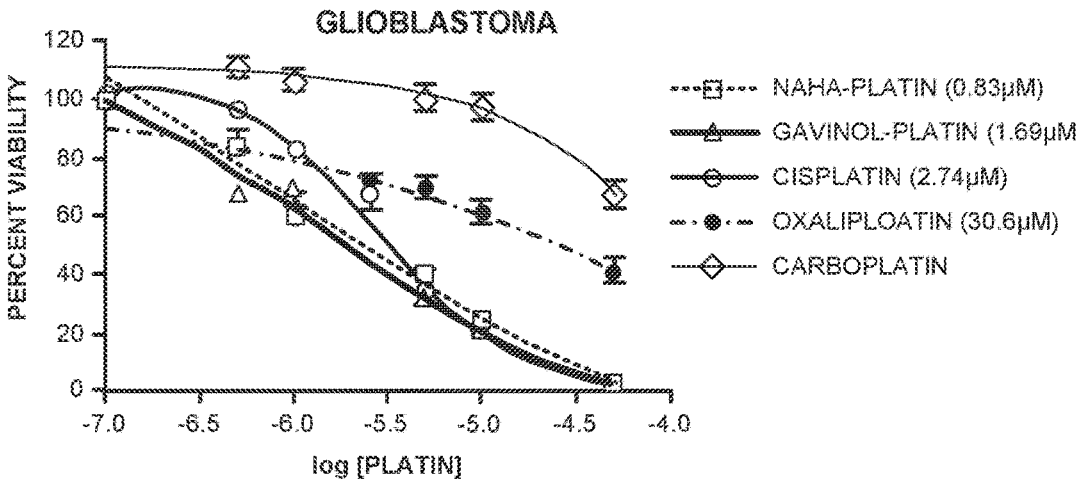
FIG. 6A-6C are representative graphs depicting the ability of enol-Pt based compounds to prevent cytotoxicity without minimizing the chemotherapeutic effects of CisPt, CarboPt, and OxaliPt in neonatal DRG cells and hepatocyte cells, respectively.
Figure 6B:
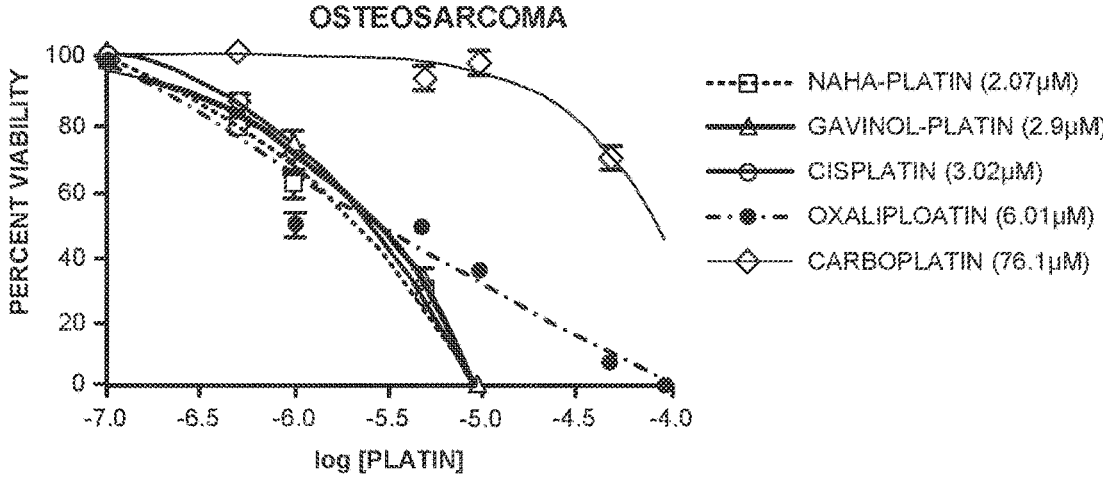
Figure 6C:
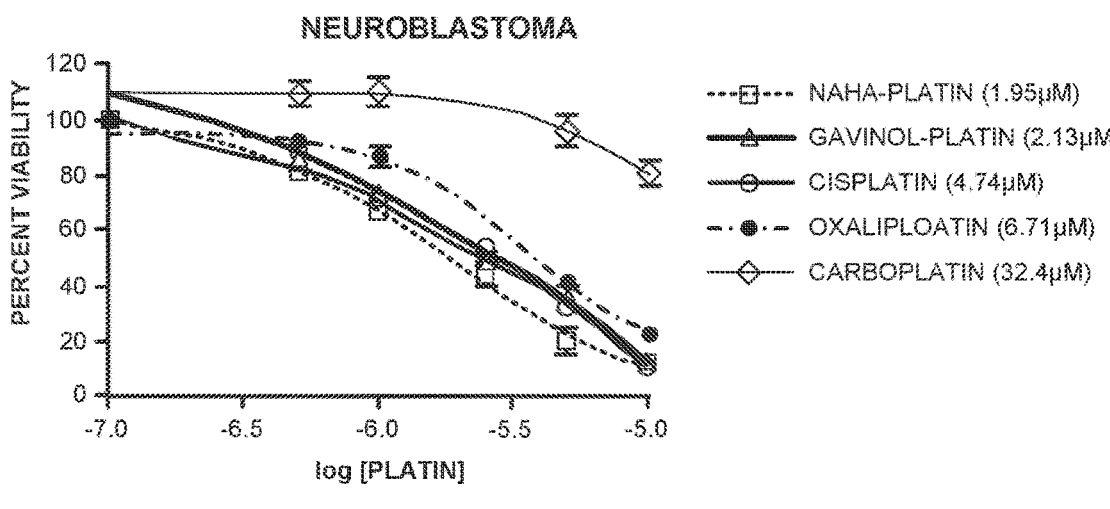

Additional experiments were conducted to determine the effect of first incubating NAHA or gavinol with CisPt for 30 min prior to exposure to the different cell lines (FIG. 6A-6C). The results indicate that the presumed CisPt-enol complex formation (e.g., NAHA-Pt; Gavinol-Pt) did not modify the antineoplastic activity of CisPt compounds in glioblastoma (FIG. 6A), osteosarcoma (FIG. 6B) or neuroblastoma (FIG. 6C) cancer cells. However, CarboPt, and to a lesser extent OxaliPt, both exhibited reduced cancer cell lethality. It is contemplated that the reduced efficacy is related to the lower electrophilicities of CarboPt and OxaliPt (Table 1).

Drug Development

Having established the efficacy of using enol compounds as neuroprotectants, the next phase of the study was considered the potential to use the enol compounds for drug development.

Relevant to drug development, the enolate-forming compounds are relatively water soluble, bioavailable and rapidly absorbed with a large volume of tissue distribution. The half-life is bi-phasic; i.e., first phase t1/2 is 40 mins, whereas the second phase is 11 hr. The acute animal toxicity of 2-ACP (another enol compound) and other 1,3-dicarbonyl enol chemicals is low (LD50>800 mg/kg) and longitudinal studies indicate a low incidence of systemic toxicity; e.g., 400-600 mg/kg per day for 60 days.

In addition, mouse studies showed that 2-ACP, NAHA, THA and gavinol were not toxic when tested using: (1) open field observations (FOBs) which evaluates activities such as rearing, grid crossing, time-in-center and gait; (2) balance beam which provides an analysis of gait and coordination; (3) functional observational battery that involves a detailed assessment of multiple sensory and motor parameters; e.g., anxiety, hearing and sight; and (4) treadmill analysis, which measures hindlimb muscle strength.

The enol compounds also offer advantages over thiol-based compounds for preventing and treating chemotherapeutic neuropathy and ototoxicity because unlike thiol compounds, the nucleophilic carbon atoms of enolate-forming drugs have relatively low pKa values (e.g., 2-ACP=7.8;

THA=7.7; and NAHA=7.9), which indicates that at physiological pH significantly more of the carbon compounds exist in the nucleophile state and are therefore, more effective at blocking the neurotoxicity and ototoxicity associated with chemotherapeutic agents.

Accordingly, the use of enol compounds are promising candidates for the development of drugs capable of inhibiting neuropathy and ototoxicity associated with chemotherapeutic agents.

Conclusion

Experimental evidence presented here indicates certain polyphenol derivatives (e.g., THA, NAHA or gavinol) can prevent the sensory neuropathy and ototoxicity associated with CisPt chemotherapy. The initial results from this study indicated that enol-Pt complexes form due to the interaction of soft enol ligands (e.g., NAHA, gavinol) with the soft attributes of Pt. Furthermore, due to the soft electronic profile of the enol compounds, the enols do not block the hard reactions of Pt with hard DNA targets (FIG. 2), where the hard-hard interaction is critical for mediating the DNA cross-linking which prevents transcription and thereby cause cancer cell death. It is further contemplated that the enol compounds scavenge Pt, serving as a soft surrogate target and thereby preventing soft Pt-based cytotoxicity.

The inability of the tested enols to influence the chemotherapeutic efficacy (e.g., FIG. 5) of Pt is consistent with the initial hypothesis that the reaction of a soft nucleophile (enol) with a hard electrophile (Pt) is thermodynamically unfavored. Together these findings suggest that the respective mechanisms of neurotoxicity (soft-soft reactions) and chemotherapy (hard-hard reactions) are independent and therefore separable.

The multifunctional cytoprotective properties of the polyphenol derivatives, in conjunction with their low toxicity and favorable pharmacokinetics suggest that these compounds could reduce the clinical incidence and severity of the CisPt sensory neuropathy. In turn, this could have a significant impact on the management of many types of CisPt -responsive neoplasm.

From the foregoing, it will be appreciated that specific embodiments of the invention have been described herein for purposes of illustration, but that various modifications may be made without deviating from the scope of the invention. Accordingly, the invention is not limited except as by the appended claims.

Para A. A method of treating or preventing chemotherapy-induced neuropathy and ototoxicity in a subject, the method comprising administering to the subject a therapeutically effective amount of one or more enol compounds.

Para B. A method of treating or preventing chemotherapy-induced neuropathy and ototoxicity in a subject, the method comprising administering to the subject a therapeutically effective amount of one or more enol compounds selected from the group consisting of 4-N-acetyl-2,6-dihydroxyacetaphenone (NAHA), 2',4',6'-trihydroxyacetophenone (THA), N-(4-acetyl-3,5-dihydroxyphenyl)-2-oxocyclopentane-1-carboxamide (gavinol), and 2-acetylcyclopentanone (2-ACP).

Para C. The method of Para A or B, further comprising administering a chemotherapeutic agent to the subject.

Para D. The method of Para C, wherein the chemotherapeutic agent is selected from the group consisting of Cisplatin (CisPt), Carboplatin (CarboPt), and Oxaliplatin (OxaliPt).

Para E. A method of treating cancer in a subject, the method comprising administering to the subject a chemotherapeutic agent and one or more enol compounds, wherein the subject does not exhibit chemotherapy-induced neuropathy and ototoxicity.

Para F. A method of treating cancer in a subject in need thereof, the method comprising administering to the subject a chemotherapeutic agent selected from the group consisting of Cisplatin (CisPt), Carboplatin (CarboPt), and Oxaliplatin (OxaliPt) and one or more enol compounds selected from the group consisting of 4-N-acetyl-2,6-dihydroxyacetaphenone (NAHA), 2',4',6'-trihydroxyacetophenone (THA), N-(4-acetyl-3,5-dihydroxyphenyl)-2-oxocyclopentane-1-carboxamide (gavinol), and 2-acetylcyclopentanone (2-ACP), wherein the subject does not exhibit chemotherapy-induced neuropathy and ototoxicity.

Para G. The method of any one of Paras A to E, wherein the enol compounds are selected from the group consisting of 4-N-acetyl-2,6-dihydroxyacetaphenone (NAHA), 2',4',6'-trihydroxyacetophenone (THA), N-(4-acetyl-3,5-dihydroxyphenyl)-2-oxocyclopentane-1-carboxamide (gavinol), and 2-acetylcyclopentanone (2-ACP).

Para H. The method of Para E, wherein the chemotherapeutic agent is selected from the group consisting of CisPt, CarboPt, and OxaliPt.

Para I. The method of Para A or B, where the chemotherapy-induced neuropathy and ototoxicity is caused by CisPt, CarboPt, and OxaliPt.

Para J. The method of any one of Paras C to F, the one or more enol compounds is co-administered with the chemotherapeutic agent.

Para K. The method of any one of Paras C to F, wherein the one or more enol compounds is administered before the chemotherapeutic agent.

Para L. The method of any one of Paras C to F, wherein the one or more enol compounds is administered after a chemotherapeutic agent.

Para M. The method of any one of Paras C to L, wherein the one or more enol compounds and the chemotherapeutic agent are administered intraperitoneally, orally, intravenously, intramuscularly, transdermally, intranasally, or through an osmotic mini-pump.

Para N. The method of any one of Paras C to L, wherein the one or more enol compounds and the chemotherapeutic agent are administered to the subject by different routes.

Para O. The method of any one of Paras A to N, wherein the subject has a testicular cancer, ovarian cancer, cervical cancer, breast cancer, bladder cancer, head and neck cancer, esophageal cancer, lung cancer, mesothelioma, brain tumor, neuroblastoma, non-Hodgkin's lymphoma, endometrial cancer, gastric cancer, Hodgkin's lymphoma, multiple myeloma.

Para P. The method of any one of Paras A to O, wherein the neuropathy is sensory neuropathy or neuropathy associated with dorsal root ganglion (DRG) neurons.

Para Q. The method of any one of Paras A to P, further comprising reducing one or more of paresthesia, tingling, neuropathic pain in the subject, or increasing vibratory sense in the subject.

Para R. The method of any one of Paras A to Q, wherein the subject is a pediatric subject.

Para S. The method of any one of Paras A to Q, wherein the subject is at least 60 years old.

Para T. A composition comprising a therapeutically effective amount of: (a) a chemotherapeutic agent selected from the group consisting of Cisplatin (CisPt), Carboplatin (CarboPt), and Oxaliplatin (OxaliPt); and (b) an enol compound selected from the group consisting of 4-N-acetyl-2,6-dihydroxyacetaphenone (NAHA), 2',4',6'-trihydroxyacetophenone (THA), N-(4-acetyl-3,5-dihydroxyphenyl)-2-oxocy-clopentane-1-carboxamide (gavinol), and 2-acetylcyclopentanone (2-ACP).

Para U. The composition of Para T, further comprising a pharmaceutically acceptable carrier.

Para V. The composition of Para T or U, wherein the composition is a liquid.

Para W. The composition of any one of Paras T to V, wherein the composition is encapsulated in a capsule shell.

Para X. The composition of any one of Paras T to W, wherein the composition comprises about 1 mg/ml of the chemotherapeutic agent.

Para Y. A kit comprising one or more enol compounds or derivatives thereof and a chemotherapeutic agent for use in treating or preventing chemotherapy-induced neuropathy or ototoxicity.

Para Z. The kit of Para Y, further comprising instructions of use.

Para AA. The kit of Para Y or Z, wherein the one or more enol compounds or derivatives thereof are selected from the group consisting of 4-N-acetyl-2,6-dihydroxyacetaphenone (NAHA), 2',4',6'-trihydroxyacetophenone (THA), N-(4-acetyl-3,5-dihydroxyphenyl)-2-oxocyclopentane-1-carbox-amide (gavinol), and 2-acetylcyclopentanone (2-ACP).

Para AB. The kit of any one of Paras Y to AA, wherein the chemotherapeutic agent is selected from the group consisting of Cisplatin (CisPt), Carboplatin (CarboPt), and Oxaliplatin (OxaliPt).

REFERENCES

1. Carozzi V A, Canta A and Chiorzaai A. (2015) Chemotherapy-induced peripheral neuropathy: What do we know about mechanism? *Neurosci. Lett.* 596: 90-107.
2. Miltenburg N C and Boogerd W. (2014) Chemotherapy-induced neuropathy: a comprehensive survey. *Can. Treat. Rev.* 40: 872-882.
3. Neuwelt E A, Brummett R E, Doolittle N D, Muldoon L L, Kroll R A, Pagel M A, Dojan R, Church V, Remsen L G and Bubalo J S. (1998) First evidence of otoprotection against carboplatin-induced hearing loss with a two-compartment system in patients with central nervous system malignancy using sodium thiosulfate. *J. Pharmacol. Exp. Ther.* 286: 77-84.
4. Carozzi VA, Marmiroli P, Cavaletti G. (2010). The role of oxidative stress and anti-oxidant treatment in platinum-induced peripheral neurotoxicity. *Curr. Cancer Drug Targets* 10: 670-682.
5. Cece R, Petruccioli M G, Cavletti G, Barajon I , Tredici G (1995) An ultrastructural study of neuronal changes in dorsal root ganglia (DRG) of rats after chronic cisplatin administration. *Histo. Histopathol.* 10: 837-845.
6. Cece R, Petruccioli M G, Pizzini G, Cavletti G,Tredici G (1995) Ultrastructural aspects of DRG satellite cell involvement in experimental cisplatin neuropathy. *Submicro. Cytol. Pathol.* 27: 417-425.
7. McKeage M J, Hsu T, Screnci K, Haddad G, Baguley B C. (2001). Nucleolar damage correlates with neurotoxicity induced by different platinum drugs. *British J. Cancer* 85: 1219-1225.
8. Brock P R, Knight K R, Greyer D R et al. (2012) Platinum-induced ototoxicity in children: A consensus review on mechanisms, predisposition and protection including a new international society of pediatric oncology Boston ototoxicity scale. *J. Clin. Oncology* 30:2408-2417.

9. Rybak L P, Whitworth C A, Mukherjea and Ramkumar V (2007) Mechanism of cisplatin-induced ototoxicity and prevention. *Hearing Res.* 226: 157-167.
10. Seretny M, Currie G L, Sena E S, Ramnarine S, Grant Ret al. (2014) Incidence, prevalence and predictors of chemotherapy-induced peripheral neuropathy: A systematic review and meta-analysis. *Pain* 155: 2461-2470.
11. Muscella A, Calabriso N, Vetrugno C, Urso L, Fanizzi FP, De Pascal' SA, Marsigliante S. (2010) Sublethal concentrations of the platinum (II) complex [Pt(O,O'-acac) (7-acac) (DMS)] alter the motility and induce anoikis in MCF-7 cells. *Brit. J. Pharmacol.* 160: 1362-1377.
12. Thompson S W, Davis L E, Kornfeld M, Hilgers R D, Standefers J C. (1984) Cisplatin neuropathy: clinical, electrophysiologic, morphologic and toxicologic studies. *Cancer* 54: 1269-1275.
13. Omar H A, Mohamed W R, Arafa S A, Shehata B A, El Sherbiny G A, Arab H H and Elgendy A N (2016) Hesperiden alleviates cisplatin-induced hepatotoxicity in rats without inhibition of its antitumor activity. *Pharmacol. Rep.* 68: 349-356.
14. LoPachin R M, Gavin T, DeCaprio A P, Barber D S (2012). Application of the hard and soft, acids and bases (HSAB) theory to toxicant-target interactions. *Chem. Res. Toxicol.* 25, 231-251.
15. LoPachin R M and Gavin T (2012) Molecular Mechanism of Acrylamide Neurotoxicity: Lessons Learned from Organic Chemistry. *Environ. Health* 120: 1650-1657.
16. LoPachin R M and Gavin T (2012) Molecular Mechanisms of Aldehyde Toxicity: A Chemical Perspective. *Chem. Res. Toxicol.* 27: 1081-1091.
17. Ballantyne B, Cawley T J (2001) 2,4-Pentanedione: toxicology update. *J. Appl. Toxicol.* 21, 165-171.
18. Beaty, J. A. and Jones, M. M. (1992) Rates of substitution by sulfur nucleophiles in cis-diamminebis (quanosine) platinum (II) chloride. *Inorg. Chem.* 31: 2547-2551.
19. Begum, A. N., Jones, M. R., Lim, G. P. et al. (2008) Curcumin structure-function, bioavailability and efficacy in models of neuroinflammation and Alzheimer's disease. *J. Pharamacol. Exp. Ther.* 326, 196-208.
20. Berndtsson M, Hagg M, Panaretakis T, Havelka A M, Shoshan M C, Linder S. (2006) Acute apoptosis by cisplatin requires induction of reactive oxygen species but is not associated with damage to nuclear DNA. *Int. J. Cancer* 120: 175-180.
21. Bug T and Mayr H (2003) Nucleophilic reactivities of carbonations in water: the unique behavior of the malodinitrile anion. *J. Am. Soc. Chem.* 125, 12980-12986.
22. Cavaletti G, Tredici G, Marmiroli P, Petruccioli M G, Barajon I, Fabbrica D. (1992) Morphometric study of the sensory neuron and peripheral nerve changes induced by chronic cisplatin (DDP) administration in rats. *Acta. Neuropathol.* 84:364-371.
23. Cervellini I, Bello E, Frapolli R, Porretta-Serapiglia C, Oggioni N et al. (2110) The neuroprotective effect of erythropoietin in docetaxel-induced peripheral neuropathy causes no reduction of antitumor activity in 13762 adenocarcinoma-bearing rats. *Neurotox. Res.* 18: 151-160.
24. Dedon P C, Borch R F. (1987) Characterization of the reactions of platinum antitumor agents with biologic and nonbiologic sulfur-containing nucleophiles. *Biochem. Pharamcol.* 36: 1955-1964.

25. DePascali S A, Papadia P, Ciccarese A, Pacifico C and Fanizzi F P (2005) First Examples of D-diketonate platinum(II) complexes with sulfoxide ligands. *Eurp. J. Inorg. Chem.* 5: 788-796.

26. Eames J (2009) Acid-base properties of enols and enolates. The Chemistry of Metal Enolates (Zablicky J ed) Chapter 8, pp 411-460. John Wiley & Sons, West Sussex, England.

27. Feghali J G, Liu W, Van de Water T R. (2001) L-N-acetyl-cysteine protection aginast cisplatin-induced auditory neuronal and hair cell toxicity. *The Laryngoscope* 111: 1147-115.

28. Fuertes M A, Alonso C J, Perez J M. (2003) Cisplatin biochemical mechanism of action: from cytotoxicity to induction of cell death through interconnections between apoptotic and necrotic pathways. *Curr. Med. Chem.* 10: 257-266.

29. Gandara D R, Wiebe V J, Perez E A, Makuch R W and DeGregorio M W (1990) Cisplatin rescue therapy: experience with sodium thiosulfate, WR2721 and diethyldithiocarbamate. *Crit. Rev Oncol/Hematol* 10: 353-365.

30. Gaona-Gaona L, Molina-jijon E, Tapia E, Zazueta C, Hernandez-Pando R, Clderon-Oliver M, Zarco-Marquez G, Pinzon E, Pedraza-Chaverri J. (2011). Protective effect of sulforaphane pretreatment against cisplatin-induced liver and mitochondrial oxidant damage in rats. *Toxicology* 286: 20-27.

31. Geohagen B C, Vydyanathan A, Kosharskyy B, Shaparin N, Gavin T and LoPachin R M. (2016) Enolate-forming phioretin pharmacophores: Hepatoprotection in an experimental model of drug-induced toxicity. *J. Pharmacol. Exp. Ther.* 357: 1-11.

32. Jamieson E R, Lippard S J (1999) Structure, recognition and processing of cisplatin-DNA adducts. *Chem. Rev.* 99: 2467-2498.

33. Kosharskyy B, Vydyanathan A, Zhang L, Shaparin N, Geohagan B C, Bivin W, Liu Q, Gavin T and LoPachin R M (2015) 2-Acetylcyclopentanone, an Enolate-Forming 1,3-dicarbonyl compound, is Cytoprotective in Warm Ischemia-Reperfusion Injury in Rat Liver. *J. Pharmacol. Exp. Ther.* 353: 150-158.

34. Lemaire M A, Schwartz A, Rahmouni R, Leng M. (1991) Interstrad cross-links are preferentially formed at the d(GC) sites in the reaction between cis-diamminedichloroplatinum(II) and DNA. *Proc. Nat. Acad. Sci.* 88: 1982-1985.

35. LoPachin, R. M. and Barber, D. S. (2006) Synaptic cysteine sulfhydryl groups as targets of electrophilic neruotoxicants. *Tox. Sci.* 94, 240-255.

36. LoPachin R M, Barber D S, Geohagen B C, Gavin T, Das S, He D. (2007) Structure-Toxicity Analysis of Type-2 Alkenes: Synaptosomal Neurotoxicity. *Toxicol. Sci.* 95, 136-146.

37. LoPachin R M, Geohagen B C, Gavin T, Das S. (2007) Neurotoxic Mechanisms of Electrophilic Type-2 Alkenes: Soft-Soft Interactions Described by Quantum Mechanical Parameters. *Toxicol. Sci.* 98: 561-570.

38. LoPachin, R. M., Barber, D. S. and Gavin, T. (2008). Molecular mechanisms of the conjugated ot,p-unsaturated carbonyl derivatives: relevance to neurotoxicity and neurodegenerative diseases. *Tox. Sci.* 104, 235-249.

39. LoPachin, R. M., Gavin, T., and Geohagen, B. C. (2009) Synaptosomal Toxicity and Nucleophilic Targets of 4-Hydroxy-2-Nonenal. *Toxicol. Sci.* 107, 171-181.

40. LoPachin R M, Gavin T, Geohagen B C, Zhang L, Casper D, Lekhraj R, Barber D S. (2011) 0-Dicarbonyi enolates: a new class of neuroprotectants. *J. Neurochem.* 116, 132-143.

41. Loudon G M (2002) Chemistry of enolate ions, enols and alpha(3-unsaturated carbonyl compounds. In Organic Chemistry, 4th ed. Chapt. 22, pp 997-1068. Oxford University Press, NY.

42. Luo J, Tsuji T, Yasuda H, Sun Y, Fujigaki Y., Hishida Y. (2008). The molecular mechanisms of the attenuation of cisplatin-indcued acute renal failure by N-acetylcysteine in rats. *Nephrol Dial Transplant* 23:2198-2205.

43. Mandic A, Hansson J, Linder S, Shoshan M C. (2003) Cisplatin induces endoplasmic reticulum stress and nucleus-independent apoptotic signaling. *J. Biol. Chem.* 278: 9100-9106.

44. Martyniuk, C. J., Fang, B., Koomen, J. M., Gavin, T., Barber, D. S. and LoPachin, R. M., (2011) Molecular Mechanism of Protein Inactivation by o.,[3-Unsaturated Carbonyl Derivatives. *Chem. Res. Toxicol.* 24, 2302-2311.

45. Muldoon L L, Pagel M A, Droll R A, Brummett R E, Doolittle N D, Zuhowski E G, Egorin M J and Neuwelt E A (2000) Delayed administration of sodium thiosulfate in animal models reduces platinum ototoxicity without reduction of antitumor activity. *Clin. Cancer Res.* 6: 309-315.

46. Muldoon L L, Walker-Rosenfeld S L, Hale C, Purcell S E, Bennett, L C and Neuwelt E A (2001) Rescue from enhanced alkylator-induced cell death with low molecular weight sulfur-containing chemoprotectants. *J. Pharmacol Exp Ther.* 6: 797-805.

47. Park S B, Goldstein D, Krishnan A V, Lin C S Y, Friedlander M L et al. (2013) Chemotherapy-induced peripheral neurotoxicity: A critical Analysis. 63: 419-437.

48. Rezk B M, Haenen G R M M, van der Vijgh W J F and Bast A. (2002) The antioxidant activity of phloretin: the disclosure of a new antioxidant pharmacophore in flavonoids. *Biochem. Biophys. Res. Comm.* 295: 9-13.

49. Sheikh-Hamad D. (2008) Cisplatin-induced cytoxicity: is the nucleus relevant? *Am. J. Physiol Renal Physiol.* 295: F42-F43.

50. Sorenson C M, Eastman A. (1988). Mechaism of cis-diamminedichloroplatinum (II)-induced cytotoxicity: role of G2 arrest and DNA double-strand breaks. *Cancer Res.* 48: 4484-4488.

51. Ta L E, Espeset L, Podratz J, Windebank A. (2006) Neurotoxicity of oxaliplatin and cisplatin of rat dorsal root ganglion neurons correlates with platinum-DNA binding. *Neuro. Toxicology* 27: 992-1002.

52. Terhegeen P M A B, Van der Hoop R G, Floot B G J, Gispen W H. (1989) Cellular distribution of cis-diamminedichloroplatinum(II)-DNA binding in rat dorsal root spinal ganglia: effect of the neuroprotecting peptide ORG.2766. *Toxicol. Appl. Pharmacol.* 99: 334-343.

53. Tomiwa, K, Nolan C, Cavanagh J B. (1986) The effects of cisplatin on rat spinal ganglia: a study by light and electron microscopy and by morphometry. *Acta. Neuropath.* 69: 295-308.

54. Wang K, Lu J, Li R. (1996) The events that occur when cisplatin encounters cells. *Coordin. Chem. Rev.* 151: 53-88.

55. Geohagen B C, Korsharskyy B, Vydyanatha A, Nordstoem L U and LoPachin R M. (2018) Phloretin pharmacology and toxicology. *Chem. Biol. Inter.* 296: 117-123.

56. Will, J., Wolters, D A, Sheldrick, W S (2008) Characterisation of cisplatin binding sites in human serum proteins using hyphenated multidimensional liquid chromatography and ESI tandem mass spectrometry. *Chem. Med. Chem.,* 3: 1696-1707.

57. Wolters D A, Washburn M P, Yates J R, III (2001) An automated multidimensional protein identification technology for shotgun proteomics. *Anal. Chem.* 73: 5683-5690.

58. Wu F, Megyesi J, Price P M. (2008) Cytoplasmic initiation of cisplatin cytotoxicity. *Am. J. Physiol. Renal Pysiol.* 295: F44-F52.

59. Zhang L, Gavin T, Geohagen B C, Liu Q, Downe K J and LoPachin R M. (2013). Protective properties of 2-acetylcyclopenanone in a mouse model of acetaminophen hepatotoxicity. *J. Pharmacol. Exp Ther.* 346: 1-11.

60. LoPachin R M, Geohagen B C, Nordstrom L U and Gavin T. (2016) Enolate-forming compounds as a novel approach to cytoprotection. *Chem. Res. Toxicol.* 29: 2096-2107.

61. Kanat O, Ertas H, Caner B (2017) Platinum-induced neurotoxicity: A review of possible mechanisms. *World J. Clin. Oncol.* 8: 329-335.

62. Avan A, Postma T J, Ceresa C, Avan A et al. (2015) Platinum-induced neurotoxicity and preventive strategies: past, present and Future. *The Oncol* 20: 411-432.

63. Callejo A, Durochat A, Bressieux S, Saleur A et al. (2017) Dose-dependent cochlear and vestibular toxicity of tran-tympaic cisplatin in the rat. *Neurotoxicology* 60: 1-9.

64. Brock P R, Knight K R, Freyer D R (2012) Platinum-induced ototoxicity in children: a consensus review on mechanism predisposition and protection, including a new international society of pediatric oncology Boston ototoxicity scale. *J. Clin. Oncol.* 30: 2408-2417.

65. Reedijk J (1999) Why does cisplatin reach guanine-N7 with competing S-donor ligands available in the cell? *Chem. Rev.* 99: 2499-2510.

66. Bazzini P and Wermuth C G in The Practice of Medicinal Chemistry 2015 4th Edition, pg 346-375.

67. Tien M, Bucher J R and Aust S D (1982) Thiol-dependent lipid peroxidation. *Biochem. Biophys. Res. Comm.* 107: 279-285.

68. Mundy R (1989) Toxicity of thiols and disulphides: involvement of free-radical species. *Free Rad. Biol. Med.* 7: 659-673.

69. Lu Y and Cederbaum Al (2006) Cisplatin-induced hepatotoxicity is enhanced by elevated expression of cytochrome P450 2E1. *Toxicol. Sci.* 89: 515-523.

70. Pinata 0, Musetti C and Sissi C (2014) Pt-Based Drugs:Tthe Spotlight Will be on Proteins. *Metallomics* 6: 380-395.

What is claimed is:

1. A method of treating chemotherapy-induced neuropathy and ototoxicity in a subject, the method comprising administering to the subject a therapeutically effective amount of one or more enol compounds, wherein the neuropathy is sensory neuropathy or neuropathy associated with dorsal root ganglion (DRG) neurons.

2. The method of claim 1, wherein the one or more enol compounds are selected from the group consisting of 4-N-acetyl-2,6-dihydroxyacetaphenone (NAHA), 2',4',6'-trihydroxyacetophenone (THA), N-(4-acetyl-3,5-dihydroxyphenyl)-2-oxocyclopentane-1-carboxamide (gavinol), and 2-acetylcyclopentanone (2-ACP).

3. The method of claim 1, further comprising administering a chemotherapeutic agent to the subject.

4. The method of claim 3, wherein the chemotherapeutic agent is selected from the group consisting of Cisplatin (CisPt), Carboplatin (CarboPt), and Oxaliplatin (OxaliPt).

5. The method of claim 1, wherein the chemotherapy-induced neuropathy and ototoxicity is caused by CisPt, CarboPt, or OxaliPt.

6. The method of claim 3, wherein the one or more enol compounds and the chemotherapeutic agent are administered intraperitoneally, orally, intravenously, intramuscularly, transdermally, intranasally, or through an osmotic mini-pump.

7. The method of claim 3, wherein the one or more enol compounds and the chemotherapeutic agent are administered to the subject by different routes.

8. The method of claim 1, further comprising reducing one or more of paresthesia, tingling, neuropathic pain in the subject, or increasing vibratory sense in the subject.

9. The method of claim 1, wherein the subject is a pediatric subject or at least 60 years old.

\* \* \* \* \*